US008389027B2

(12) United States Patent
Patkar et al.

(10) Patent No.: US 8,389,027 B2
(45) Date of Patent: Mar. 5, 2013

(54) DIGOXIN-LIKE FUNGAL GLYCOSIDE WITH CYTOTOXIC PROPERTIES: NOVEL ASSAY AND APPLICATIONS

(75) Inventors: Rajesh Narhari Patkar, Singapore (SG); Naweed Isaak Naqvi, Singapore (SG)

(73) Assignee: Temasek Life Sciences Laboratory, Singapore (SG)

( * ) Notice: Subject to any disclaimer, the term of this patent is extended or adjusted under 35 U.S.C. 154(b) by 0 days.

(21) Appl. No.: 12/999,768

(22) PCT Filed: Jun. 18, 2009

(86) PCT No.: PCT/SG2009/000220
§ 371 (c)(1),
(2), (4) Date: Dec. 17, 2010

(87) PCT Pub. No.: WO2009/154579
PCT Pub. Date: Dec. 23, 2009

(65) Prior Publication Data
US 2012/0003261 A1  Jan. 5, 2012

Related U.S. Application Data

(60) Provisional application No. 61/129,361, filed on Jun. 20, 2008.

(51) Int. Cl.
*A61K 36/00* (2006.01)
(52) U.S. Cl. ...................................... 424/725
(58) Field of Classification Search ............ None
See application file for complete search history.

(56) References Cited

PUBLICATIONS

Kumala et al, Cytotoxic secondary metabolites from fermentation broth of *Brucea javanica* endophytic fungus 1.2.11., Research Journal of Microbiology (2007) vol. 2, No. 8, pp. 625-631.*
Thines et al, Glisoprenins C, D and E, new inhibitors of appressorium formation in *Magnaporthe grisea*, from cultures of Gliocladium roseum. 1. Production and biological activities. The Journal of antibiotics, (Feb. 1998) vol. 51, No. 2, pp. 117-122.*
Kumala et al, cytotoxic secondary metabolites from fermentation broth of *Brucea javanica* endophytic fungus 1.2.11. Research Journal of Microbiology (2007) vol. 2, No. 8, pp. 625-631.*
Amaresh et al, Effect of some plant extracts on uredospore germination of *Puccinia helianthi* causing rust of sunflower, PL. Dis. Res. 18 (1): 88-89, 2003.*
Waterman, P.G., "Searching for Bioactive Compounds: Various Strategies," Journal of Natural Products, vol. 53, No. 1, pp. 13-22, Jan.-Feb. 1990.
McKee, T.C., "Isolation and Characterization of New Anti-HIV and Cytotoxic Leads from Plants, Marine, and Microbial Organisms," Journal of Natural Products, vol. 60, No. 5, pp. 431-438, May 1997, © Copyright 1997 by the American Chemical Society and the American Society of Pharmacognosy.
Sanchez Lopez, J.M. et al., "New Cytotoxic Indolic Metabolites from a Marine Streptomyces," Journal of Natural Products, vol. 66, No. 6, pp. 863-864, © 2003 American Chemical Society and American Society of Pharmacognosy.
Sun, C.B., "A Multidrug Resistance Transporter in Magnaporthe is Required for Host Penetration and for Survival during Oxidative Stress," The Plant Cell, vol. 18, No. 12, pp. 3686-3705, © Copyright 2006 American Society of Plant Biologists.
International Search Report, PCT/SG2009/000220, filing date: Jun. 18, 2009, 8 pages.

* cited by examiner

*Primary Examiner* — Qiuwen Mi
(74) *Attorney, Agent, or Firm* — Rothwell, Figg, Ernst & Manbeck, P.C.

(57) ABSTRACT

The present invention provides methods of isolating cytotoxic metabolites from a fungus, and specific metabolites obtained from such methods. The present invention also provides methods of controlling fungal diseases in plants by treating the plants with cytotoxic metabolites as well as methods of treating cardiac arrhythmia in organisms in need of such treatment by administering the above-noted metabolites to such organisms.

10 Claims, 20 Drawing Sheets

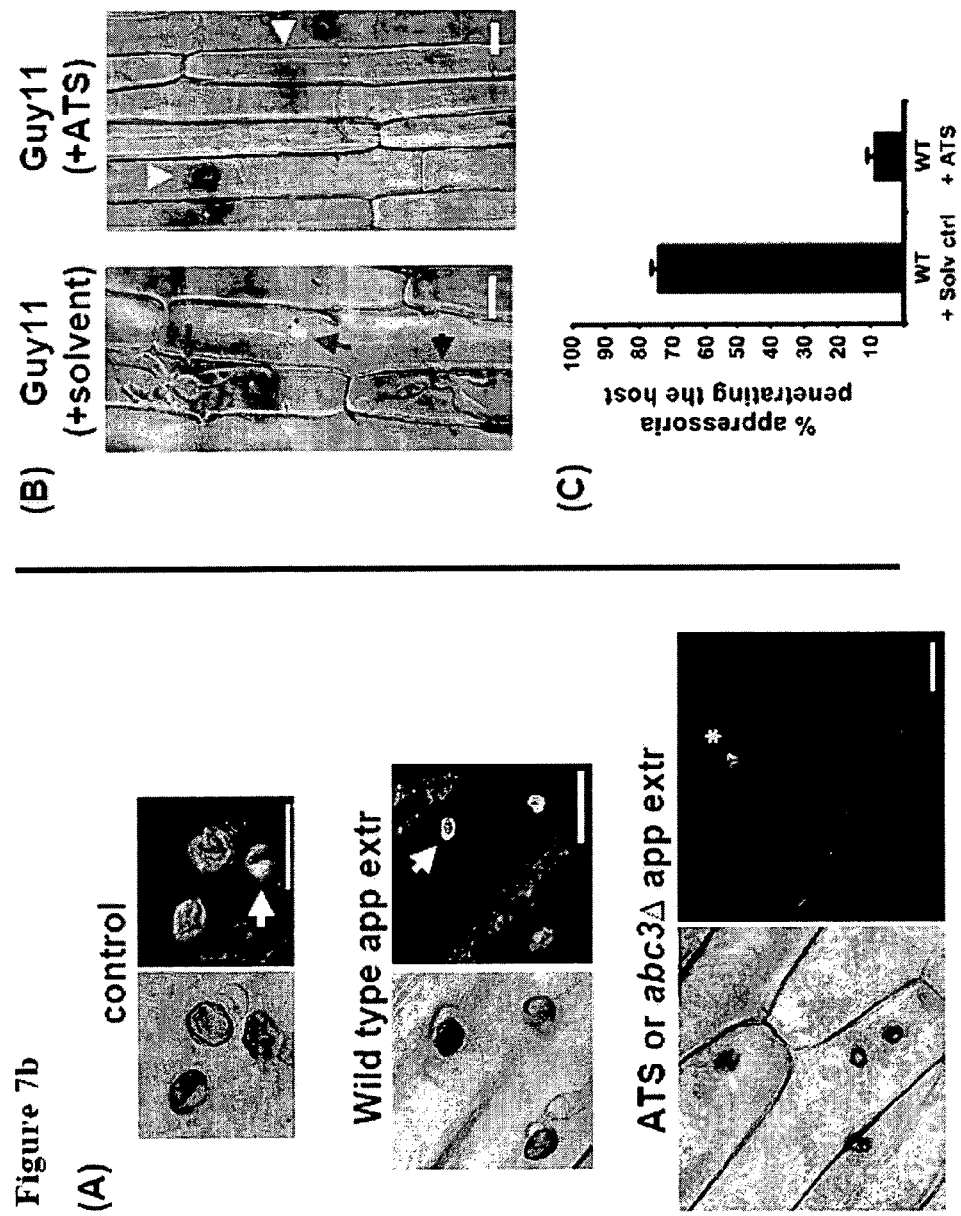

DIGOXIN-LIKE FUNGAL GLYCOSIDE WITH CYTOTOXIC PROPERTIES: NOVEL ASSAY AND APPLICATIONS

CROSS-REFERENCE TO RELATED APPLICATIONS

The present application claims benefit under 35 U.S.C. §119 of U.S. Provisional Patent Application No. 61/129,361, filed Jun. 20, 2008, which application is hereby incorporated by reference in its entirety.

FIELD OF THE INVENTION

This invention relates generally to the field of bioassays and, more particularly, to assays for isolating cytotoxic and/or antimicrobial metabolites from plant pathogens, and to various uses for such isolated compounds.

BACKGROUND OF THE INVENTION

Throughout this application, various patents, published patent applications and publications, are referenced. Disclosures of these patents, published patent applications and publications, in their entireties, are hereby incorporated by reference into this application. Included among the patents and applications incorporated by reference are U.S. Provisional Patent Application 60/782,515 and copending International Application No. PCT/SG2007/000071 (which designates the United States). In the case of conflict, the present specification, including definitions, will control. Full bibliographic citations for the publications may be found listed in the List of References immediately preceding the claims.

Natural products (NPs) are typical secondary metabolites produced by organisms in response to external stimuli, such as nutritional changes, infection, and adaptive evolution. Several different NPs produced by plants, fungi, bacteria, protozoans, insects and animals have been isolated as biologically active pharmacophores. Well-known examples of valuable NPs used widely in medical and animal health industry include lovastatin (anticholesterolemic agent), cyclosporine A and tacrolimus (immunosuppressive agents), paclitaxel and doxorubicin (antitumor agents), erythromycin (antibiotic), and amphotericin B (fungicidal agent) (Strohl 2000).

A wide variety of actinomycetes have been shown to exhibit significant antifungal activity (Lee and Hwang 2002). Likewise, filamentous fungi are also known to produce a variety of antifungal compounds, including echinocandins, ergokinin A, sphingofungin, peptaibols, and several other compounds with a diversity of core structures. A variety of pseudomonads have been shown to synthesize seed- and crop-protecting antifungals like pyrrolnitrin, syringomycin etc (Rangaswamy et al, 1998). Similarly, extracts of many plants have been shown to contain low-molecular-weight compounds, which exhibit antifungal activity in vitro. These compounds include a diverse array of secondary metabolites, such as phenolics, saponins, cyanogenic glycosides, cyclic hydroxamic acids, sesquiterpenes, isoflavonoids, sulfur-containing indole derivatives, and many other compounds (Osbourn, 1999). Flocculosin is a novel low-molecular-weight glycolipid isolated from the yeast-like fungus *Pseudozyma flocculosa*. It is used to control fungal powdery mildew disease in plants and has also been successfully tested against human fungal pathogens like *C. albicans* and *Cryptococcus neoformans* (Mimee et al, 2005).

In spite of the progress in antifungal therapy, drugs like amphotericin B or triazole have limited use because of their toxicity and/or drug resistance issues (Bagnis and Deray, 2002). Other promising candidate drugs like Caspofungin have low oral bioavailability (Boucher et al, 2004). Hence, there is a need for the isolation or synthesis of new compounds with different modes of action and low toxicity.

ATP-binding cassette (ABC) transporters, which constitute the largest superfamily of proteins known, are able to couple the hydrolysis of ATP to the transport of a variety of substrates either into or out of cells (Ritz et al. 2003). In humans, loss of ABC transporter function has been implicated in several pathologies including cystic fibrosis, cholestasis, artherosclerosis, hypoglycemia, hyperbiliruginemia, and macular dystrophy and degenerative diseases (Pastan and Gottesmann 1988). Moreover, the P-glycoprotein class of ABC transporters is able to efflux chemotherapeutic drugs and lipids, resulting in reduced effectiveness of cancer treatments (Tsuruo et al, 2003). Similarly, ABC transporters in bacteria are essential for survival and are also required to secrete toxins and antimicrobial agents (Buchaklian and Klug, 2006).

Loss-of-function analysis of ABC3, which encodes a novel multidrug resistance transporter in the cereal pathogen *Magnaporthe grisea*, showed that MDR-based efflux plays an essential role in fungal pathogenesis (Sun et al. 2006; PCT International Patent Application No. PCT/SG2007/000071). Abc3-deletion strain of *M. grisea* has been classified as a non-pathogenic mutant. Although it forms the infection structures called appressoria, the lack of infectivity in the abc3-delete mutant was correlated to its inability to penetrate the host tissue, which in turn, was proposed to be due to accumulation of an inhibitory metabolite and/or perturbed redox homeostasis within the appressoria. Further characterization confirmed that Abc3 function is required by the blast fungus to withstand cytotoxic and oxidative stress especially within the appressoria during infection.

SUMMARY OF THE INVENTION

In the present invention, it has been demonstrated that cytotoxic metabolites can be isolated from a fungus, preferably from the appressoria of the abc3Δ rice-blast fungus *Magnaporthe grisea*. In particular, a cytotoxic metabolite hereinafter referred to as Abc3 transporter substrate or "ATS" has been isolated and purified. Moreover, it has been demonstrated herein that ATS shows cytotoxic activity against different fungal species. Exogenous addition of ATS prevented the wild-type *Magnaporthe* strain from breaching the host surface and showed enhanced hypersensitive response (HR) in the host plant tissue. Moreover, treatment with the ATS molecule leads to aberrant cytokinesis and morphogenesis in yeasts, such as *S. pombe* and *C. albicans*. It also has been shown that popular cardiac glycosides like digoxin (including lanoxin) and ouabain have potential antifungal activity in addition to already known anti-cardiac arrhythmia activity. Furthermore, it is demonstrated herein that ATS is functionally related to cardiac glycosides, such as Digoxin, and that exogenous application of ATS reduces heart rate in zebrafish.

Accordingly, the invention provides a method of isolating and guiding the purification of a cytotoxic metabolite from a fungus, said method comprising: preparing an appressorial extract from a fungus; subjecting the appressorial extract to chromatographic size fractionation to obtain one or more fractions; testing the one or more fractions for cytotoxic activity; subjecting fractions exhibiting cytotoxic activity to further chromatographic fractionation to obtain further fractions; testing the further fractions for cytotoxic activity; pooling fractions having similar cytotoxic activity; and subjecting the pooled fractions to liquid chromatography to obtain the isolated cytotoxic metabolite. The invention further provides metabolites, particularly ATS, isolated from the above methods. The invention also provides methods for controlling fungal diseases in plants, including important crop plants, by treating such plants with the isolated metabolite (ATS) or with cardiac glycosides, such as Digoxin, digoxigenin, and ouabain. Moreover, the invention provides methods of treating cardiac arrhythmia in an organism, preferably a vertebrate, by administering the isolated metabolite (e.g., ATS) to the organism.

DETAILED DESCRIPTION OF THE INVENTION

Figure 1A:
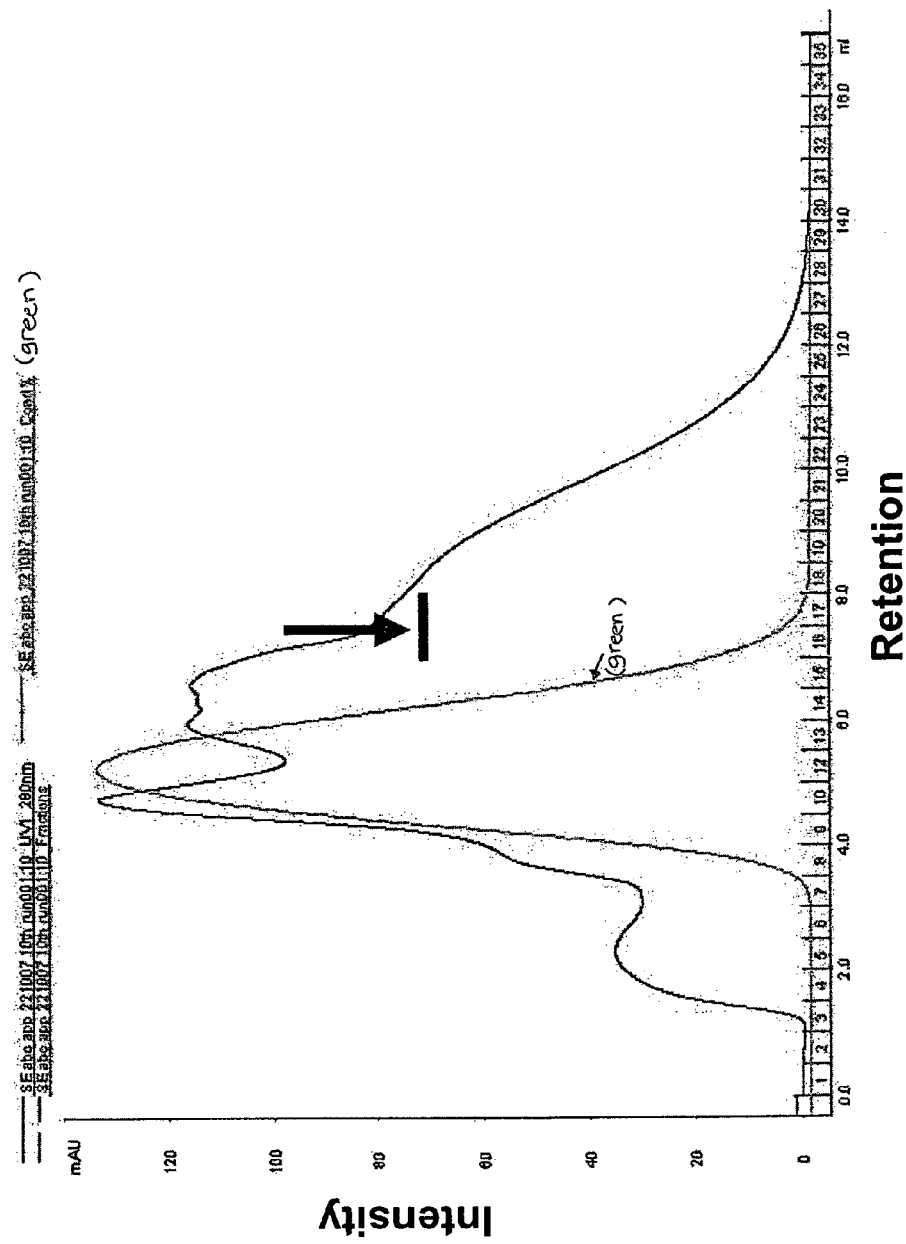
FIG. 1: Purification of ATS from abc3Δ appressoria. a) Total crude appressorial extract from abc3Δ was fractionated by size exclusion chromatography. Arrow and bar indicates fraction number 16 and 17 containing highest cytotoxic activity. b) Fraction 16 and 17 from previous run were re-fractionated by size exclusion chromatography. The bar indicates fractions 9 to 16 containing the cytotoxic activity. c) Final step of purification of ATS by liquid chromatography using a C18 RP-HPLC column. Arrowhead shows purified ATS. The chromatogram in green indicates conductivity due to the salt present in the sample.

Loss of Abc3, an MDR efflux pump essential for virulence of the rice-blast fungus *Magnaporthe grisea*, leads to reduced viability and non-pathogenicity due to the accumulation of cytotoxic metabolite(s) in the infection structures. In embodiments of the present invention, a fission-yeast based novel bioassay has been established to monitor and purify such toxic metabolite(s) from the appressorial contents of the abc3Δ mutant. ATS is the first metabolite identified in *M. grisea* with inherent cytotoxic activity and shares some properties of cardiac glycosides of therapeutic importance.

In the present invention, it has been demonstrated that a cytotoxic metabolite can be isolated from a fungus, preferably from the abc3Δ appressoria of the rice-blast fungus *Magnaporthe grisea*. In particular, a cytotoxic metabolite hereinafter referred to as ABC3 transporter substrate or “ATS” has been isolated and purified. Moreover, it has been demonstrated herein that ATS shows cytotoxic activity against different fungal species. Exogenous addition of ATS prevented the wild-type *Magnaporthe* strain from breaching the host plant surface while inducing local HR-like response in the host tissue. Moreover, the ATS molecule achieves aberrant cytokinesis and morphogenesis in yeasts, such as *S. pombe* and *C. albicans*. Furthermore it has been shown that ATS is functionally related to cardiac glycosides, such as Digoxin, and that exogenous application of excess ATS specifically perturbs embryonic heart function in zebra fish. In addition, digoxin, digoxigenin, and ouabain showed antifungal activity similar to that of ATS; and digoxin reduced fungal infection in plants.

In an aspect, the present invention provides a method of isolating and guiding the purification of a cytotoxic metabolite from a fungus, the method comprising preparing an appressorial extract from a fungus; subjecting the appressorial extract to chromatographic size fractionation to obtain one or more fractions; testing the one or more fractions for cytotoxic activity; subjecting fractions exhibiting cytotoxic activity to further chromatographic fractionation to obtain further fractions; testing the further fractions for cytotoxic activity; pooling fractions having similar cytotoxic activity; and subjecting the pooled fractions to liquid chromatography to obtain an isolated cytotoxic metabolite. In preferred embodiments, the fungus is the *M. grisea* rice blast fungus, more preferably the fungus is an *M. grisea* abc3Δ strain. In preferred embodiments, the cytotoxic activity tested in the method is cytotoxic activity against *S. pombe*, but can, in alternate embodiments include, without limitation, cytotoxicity against budding yeast *Saccharomyces cerevisiae*, or *C. albicans*. Other organisms like *Neurospora crassa*, or *Ustilago maydis* can also be used for the assays.

The appressoria can be obtained through techniques familiar to those of ordinary skill in the art. For example, conidia can be harvested from fungal cultures and allowed to germinate and form mature appressoria using known techniques. Chromatography columns, nylon membrane filters, and other suitable equipment and apparatus readily familiar and available to those of skill in the art can be utilized as appropriate in the novel methods described herein.

The invention also provides a cytotoxic metabolite obtained by the methods described herein, including the method described above. In embodiments, the cytotoxic metabolite is ATS. Tandem MS data suggest that ATS is a digoxin-like cardiac glycoside. The invention also identifies previously uncharacterized antifungal activity of digoxin, digoxigenin, and ouabain.

The cytotoxic metabolite can possess broad antifungal and/or antimicrobial activity, including, but not limited to toxicity against yeasts, such as, without limitation, *S. pombe*, *C. albicans*, budding yeast *S. cerevisiae*, and others, or toxicity against a fungus, such as, without limitation, *M. grisea*.

In an aspect, the invention also provides a method of controlling a fungal disease in a plant, said method comprising treating the plant with a cytotoxic metabolite as obtained and described as above and elsewhere herein or with digoxin, digoxigenin, or ouabain. The plant can be an important crop plant, such as rice, barley, or other monocot or dicot species. The fungal disease can be one of a number of fungal diseases, including, without limitation, rice blast. Various other fungal diseases on crops can be considered for the treatment, as well, including, for example, powdery mildew in cereals, potato late blight, *Fusarium* head blight of barley and wheat, leaf rust and loose smut of wheat, and sheath blight of rice.

In embodiments, the treatment of the plant with a cytotoxic metabolite of the present invention, such as ATS, or with a steroidal glycoside, such as digoxin, digoxigenin, or ouabain, induces a hypersensitive response in the plant. In alternate embodiments, the treatment causes inhibition of host penetration by the targeted fungal pathogen. Methods of treating plants to achieve disease control are well known in the art, and can include, for example, spraying.

The present invention also provides a method of treating cardiac arrhythmia in an organism in need of such treatment, by administering the cytotoxic metabolite obtained and described as herein, to the organism. The metabolite is preferably ATS. The organism is preferably a mammal, more preferably a human. The administration can be by any mode known to those of ordinary skill in the art. Preferable modes of administration are oral and intravenous.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., *Molecular Cloning* (Cold Spring Harbor Laboratory Press, Cold Spring Harbor, N.Y., 1982); Sambrook et al., *Molecular Cloning, 2nd Ed.* (Cold Spring Harbor Laboratory Press, Cold Spring Harbor, N.Y., 1989); Sambrook and Russell, *Molecular Cloning, 3rd Ed.* (Cold Spring Harbor Laboratory Press, Cold Spring Harbor, N.Y., 2001); Ausubel et al., *Current Protocols in Molecular Biology* (John Wiley & Sons, updated through 2005); Glover, *DNA Cloning* (IRL Press, Oxford, 1985); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, *Antibodies*, (Cold Spring Harbor Laboratory Press, Cold Spring Harbor, N.Y., 1998); Jakoby and Pastan, 1979; *Nucleic Acid Hybridization* (B. D. Hames & S. J. Higgins eds. 1984); *Transcription And Translation* (B. D. Haines & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, (Blackwell Scientific Publications, Oxford, 1988); Hogan et al., *Manipulating the Mouse Embryo*, (Cold Spring Harbor Laboratory Press, Cold Spring Harbor, N.Y., 1986); Westerfield, M., *The zebra fish book. A guide for the laboratory use of zebra fish* (*Danio rerio*), 4th Ed., (Univ. of Oregon Press, Eugene, Oreg., 2000).

EXAMPLES

In light of the preceding description, one of ordinary skill in the art can practice the invention to its fullest extent. The present invention is further described by reference to the following Examples, which are offered by way of illustration and are not intended to limit the invention in any manner. Standard techniques well known in the art, or the techniques described below were utilized.

Example 1

Methodology for the Isolation of ATS from abc3Δ Strain of *M. grisea*

Conidia were harvested from 8 to 9 day old fungal cultures (abc3Δ strain) and suspended in de-ionized water to get a count of approximately $1 \times 10^6$ conidia per ml. *Magnaporthe* abc3Δ and the *S. pombe* MBY2838 strain discussed herein (including throughout the various Examples and other disclosure) can be easily made by one of ordinary skill in the art using routine experimental protocols (detailed in Sun et al., 2006) and the requisite gene sequences available in the public domain [Genbank accession #DQ156556 (ABC3) and SPCC663.03 (PMDI)]. Two hundred microlitres each of such conidial suspension was placed on to a glass coverslip and the conidia were allowed to germinate and form mature appressoria over 24 h under high humidity. At the end of incubation period, the liquid from the coverslips was collected as supernatant. The appressoria on each coverslip were covered with 100 µl of 0.5 M solution of NaCl and incubated for 5 h in dark under humid conditions. Appressorial content together with the hypertonic solution was collected and saved as "appressorial extract". A cell scraper was used to collect the appressorial debris attached to the coverslips. Such total appressorial extract was lyophilized and the concentrated appressorial extract was filtered through 0.2 μm nylon membrane filter and size-fractionated and desalted using a Hi-Trap column (GE Healthcare Life Sciences, Sweden) as per the manufacturer's instructions. Elution was performed with sterile de-ionized water with the flow rate set at 1 ml/min. Eluate was collected as 0.5 ml fractions. The whole set up used for this chromatographic elution was that for Fast Performance Liquid Chromatography using Akta Purifier 10 (Amersham, GE Healthcare, Sweden). Fraction(s) showing cytotoxic activity against fission yeast was re-loaded onto the same 'Hi-Trap' desalting column for further separation. The fraction(s) with the same cytotoxic activity was collected, pooled, and loaded onto a C18 reverse phase HPLC column (Phenomenex, USA). The mobile phase used for elution was 30% acetonitrile with 0.1% formic acid and the elution was carried out under isocratic conditions with 0.5 ml/min flow rate and 0.5 ml fraction volume. The fraction corresponding to a single peak was ascertained to possess the characteristic cytotoxic activity and was subsequently used as purified ATS for further characterization and molecular identification.

Example 2

In vitro Analysis of ATS Antifungal Activity Against Fission Yeast

Approximately, 3 μl of 1×10$^7$ cells/ml from overnight grown wild-type *S. pombe* culture MBY104 or MBY2838 strain expressing *M. grisea* ABC3 (pmd1::URA4; MgABC3$^+$) was inoculated in 150 μl fresh YES medium in a 96 well plate. The cells were incubated at 25° C. on a rocking platform in presence of 50 μl of de-ionised water (untreated) or 10 ng of purified ATS (treated). Cell density of untreated or treated wild-type yeast cells was checked in terms of absorbance after every one hour over 5 to 6 generations. For microscopic observation of untreated and treated samples, the cells were harvested, washed, stained with calcofluor white after 6 h of incubation, and examined by epifluorescent illumination (360 nm excitation) on an Olympus IX71 microscope. Effect of ATS on karyogamy or mitosis was studied by using an *S. pombe* strain MBY816; (Wang et al., 2002), where the cells were treated as described above and GFP epifluorescence examined (488 nm excitation) using an Olympus IX71 microscope. Experiments were performed in triplicate and confirmed by several biological replicates. The *S. pombe* strain MBY816 can be easily made by using sequence information in the public domain (Genbank accession #SPAC1834.04, Accession no. P09988) and the protocols detailed in Wang et al., (2002).

Example 3

Estimation of Minimum Inhibitory Concentration (MIC) of Digoxin, Digoxigenin, and Ouabain For *S. pombe*

Approximately, 1×10$^7$ cells/ml from overnight grown culture of MBY 104 was inoculated in 20 ml fresh YES medium in 250 ml flasks. The cells were incubated at 25° C. on a shaker in absence or presence of different concentrations of digoxin. A stock of 1 mM standard glycosides (Sigma Aldrich, USA) was prepared by adding 7.8 mg, 3.9 mg, and 7.28 mg of digoxin, digoxigenin, and ouabain, respectively, in 10 ml of 50% ethanol. A working stock of 200 μM solution was prepared by diluting 1 mM stock with fresh YES medium. Further dilutions were made from this working stock by adjusting total volume with YES to 20 ml. Cell density of untreated or treated wild-type yeast cells was checked in terms of absorbance after every one hour over 5 to 6 genera-tions. Experiments were performed in duplicate each time and confirmed by several biological replicates.

Example 4

*C. albicans* Growth Inhibition Assays

*C. albicans* strain SC5314 (a kind gift from Y. Wang, Singapore) was grown in YPD broth over night at room temperature. Approximately, 3 μl of 1×10$^7$ cells/ml culture was inoculated in 150 μl of fresh YPD medium dispensed in a 96-well plate. The yeast cells were treated in a similar way as *S. pombe* above. For induction of hyphal growth in *Candida* strain, 10% calf serum was added to the YPD medium and the cells were grown at 37° C. for 6 h with or without ATS. For microscopic observation of untreated and treated samples (both yeast as well as hyphae), the cells were harvested, washed, and stained with calcofluor white after 6 h of incubation.

Example 5

*M. grisea* Growth Assays

To study the effect of ATS on germinating wild-type *M. grisea* (Guy11), 1 μl of a conidial suspension (ca. 1×10$^6$ conidia/ml) was mixed with 20 μl of water or purified ATS and drop-inoculated onto 0.6% agarose and incubated for 2-3 h. Untreated or treated cells were stained with calcofluor white, washed and observed using epifluorescence microscopy mentioned above.

Example 6

Host Leaf Penetration Assays

Approximately 1000 conidia from the wild-type Guy11 strain per spot inoculation (~20 μl) were used to test penetration of either rice leaf sheath or onion epidermis. Twenty microlitre of sterile de-ionised water (control) or purified ATS (~5 ng) was mixed with 2 μl of conidial suspension (approximately 1000 conidia) and inoculated onto rice leaf sheath or onion epidermis and incubated for 24-30 h under humid conditions. Fungal invasion of the host tissue was quantified by counting penetration pegs using aniline blue staining of papillary callose deposits within the host tissue, and by counting appressoria showing penetration hyphae (DIC imaging). Callose papillae were observed by epifluorescent illumination (360 nm excitation) on an Olympus IX71 microscope.

Example 7

Surface Inoculation Assays on Leaf Explants

A 20 μl drop of sterile de-ionised water or purified ATS was inoculated onto rice or barley leaf blade and incubated for 48 to 72 h. Barley leaf blades incubated for 72 h were tested for cell viability by staining with Trypan blue. Rice leaf blades inoculated for 48 h were examined for $H_2O_2$ production by staining with Cerium chloride ($CeCl_3$) as described earlier (Tanaka et al. 2006).

Example 8

Barley Leaf Infection Assay

Approximately 100 or 200 conidia from the wild-type Guy11 strain per spot inoculation (~20 μl) were used to study disease reaction in presence or absence of digoxin. Twenty microlitre of sterile de-ionised water (control) or standard digoxin (200 μM) was mixed with 2 μl of conidial suspension (approximately 100 or 200 conidia) and inoculated onto barley leaf blade and incubated for 5-7 days under humid conditions. Disease reaction was scored by visual observation for typical disease lesions.

Example 9

Enzyme Linked Immunosorbent Assays for Digoxin or ATS

ELISA tests were performed using a standard set of digoxin concentrations and anti-digoxin monoclonal antibodies (Sigma Aldrich, USA). Purified ATS (50 µl) or standard digoxin (6 ng to 6 µg) was coated onto ELISA plate. The wells were later blocked overnight at 4° C. with 10% calf serum in 1× PBS containing 0.05% Tween 20. Monoclonal antibodies (1:5000) against digoxin used as primary Ab were added to the wells and incubated for 2 h. After incubation, the wells were washed 4 times for 15 min each with blocking buffer used above followed by incubation with HRP conjugated anti-mouse secondary antibodies. Wells were washed in a similar way with 1× PBS containing 0.05% Tween 20 after incubation with secondary Ab for 1 h. Ready to use TMB substrate (Sigma, Aldrich, USA) was added to the wells to test HRP activity. Assays either without antigen (digoxin or ATS) or without primary antisera were run in parallel as negative controls.

Example 10

Recording of Cardiac Activity in Zebra Fish Larvae

Zebra fish (*Danio rerio*) were raised under standard laboratory conditions at 28° C. The line used was wild-type TU. A working concentration of 415 nM ATS was prepared in fish water. Embryos at 0 to 1 hpf were incubated in either ATS (100 ng/300 µl) containing water or the solvent control (prepared by using any other HPLC fraction collected during ATS purification) and observed over 3 dpf. Bright field pictures and videos (streaming with time lapse 40 msec per frame, 150 frames over 5.7 sec) were taken using Zeiss Axioplan 2 microscope equipped with a CCD camera. The heart rates (in terms of time taken in seconds to complete 20 beats) of control and treated larvae were estimated using a digital chronograph.

Example 11

*M. grisea* abc3Δ Strain Accumulates Cytotoxic Metabolite ATS

Figure 1B:
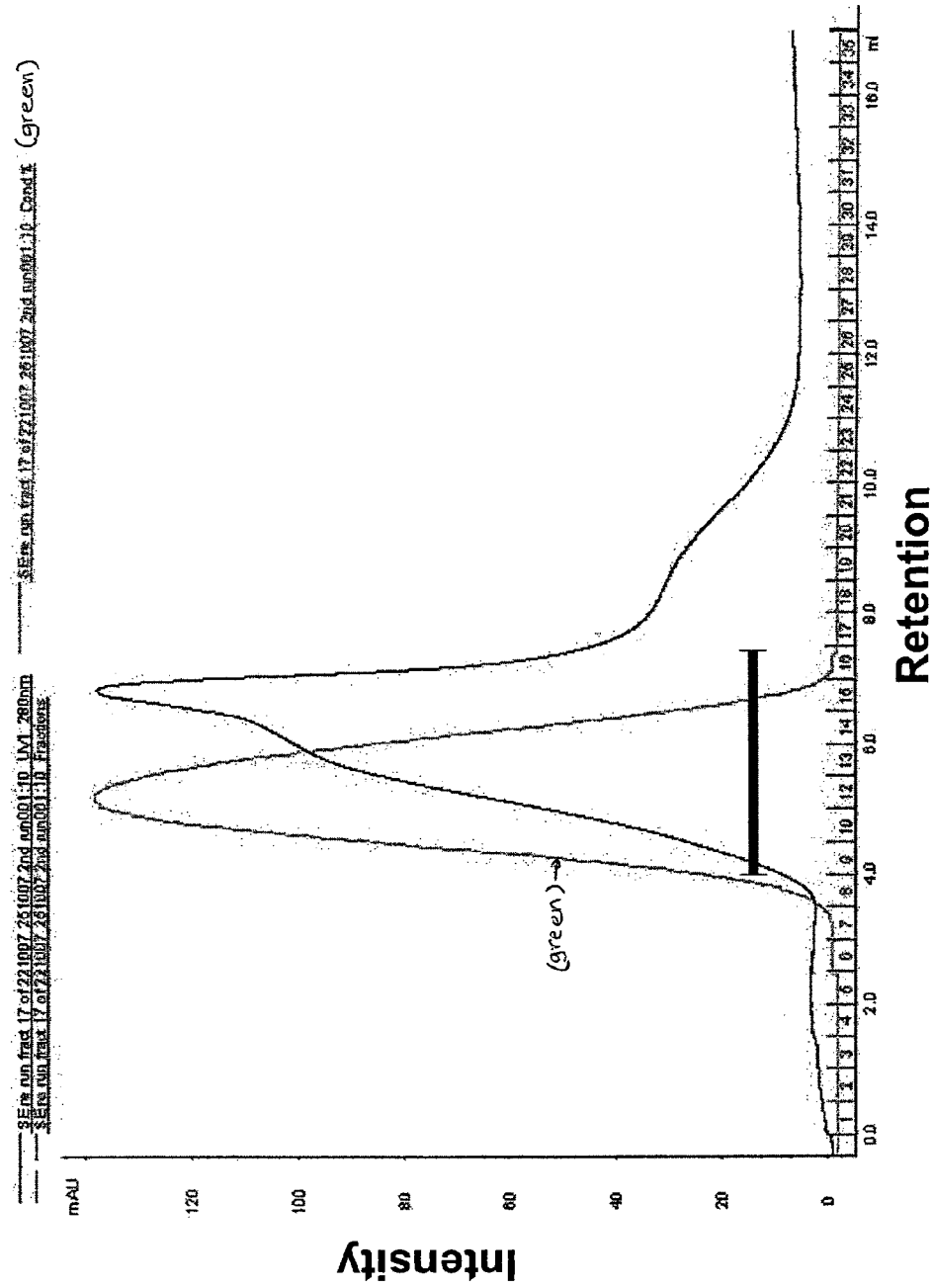
Figure 1C:
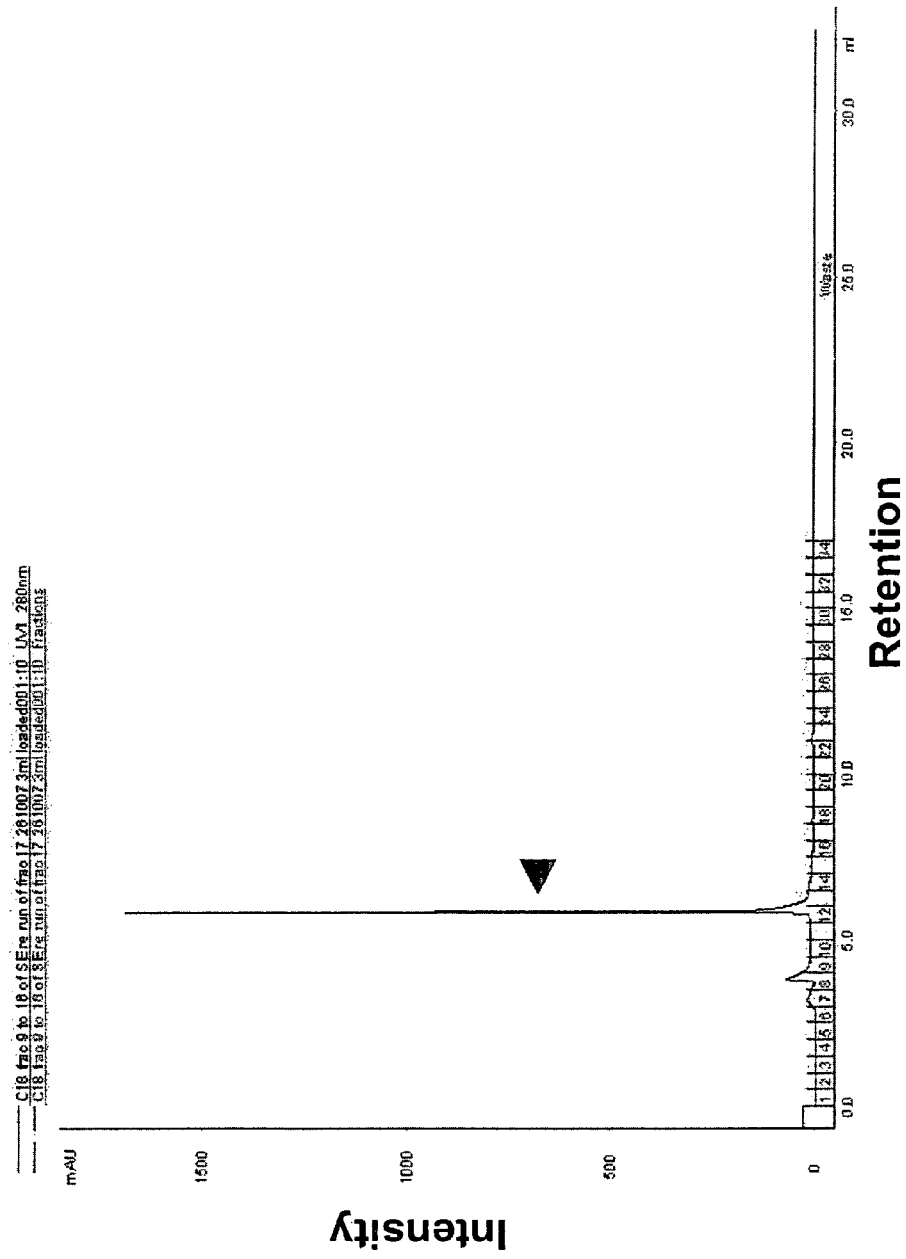
Figure 2A:
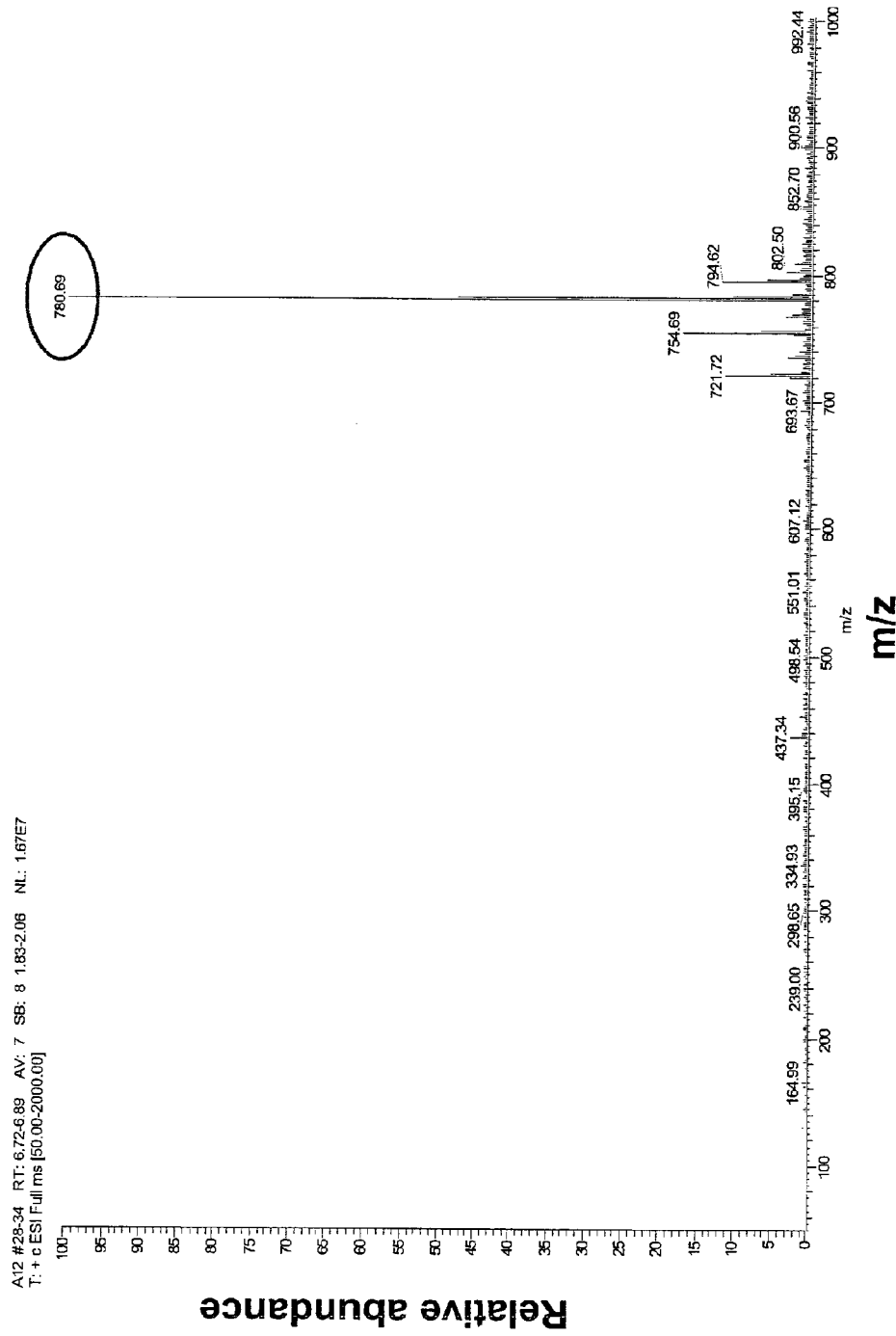
FIG. 2: ATS is a Digoxin-like glycoside. a) Molecular mass of ATS (m/z 780) was identified by mass spectrometric analysis. b) Chemical structure of Digoxin (m/z 780) that has a steroid nucleus, sugar side chain, and a lactone ring. The derivatives from ionized digoxin are indicated with their respective masses. c) ATS (m/z 780) was ionized further by ESI. Daughter ions similar to those from digoxin are encircled.
Figure 2B:
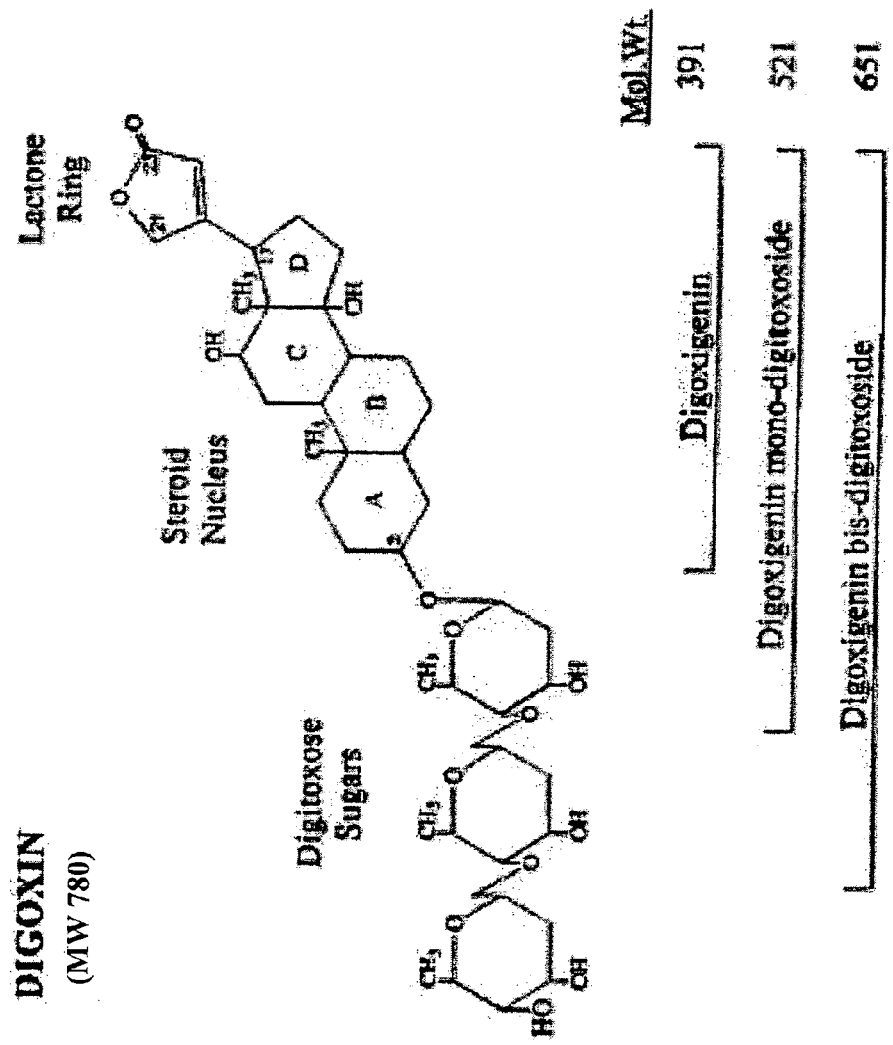
Figure 2C:
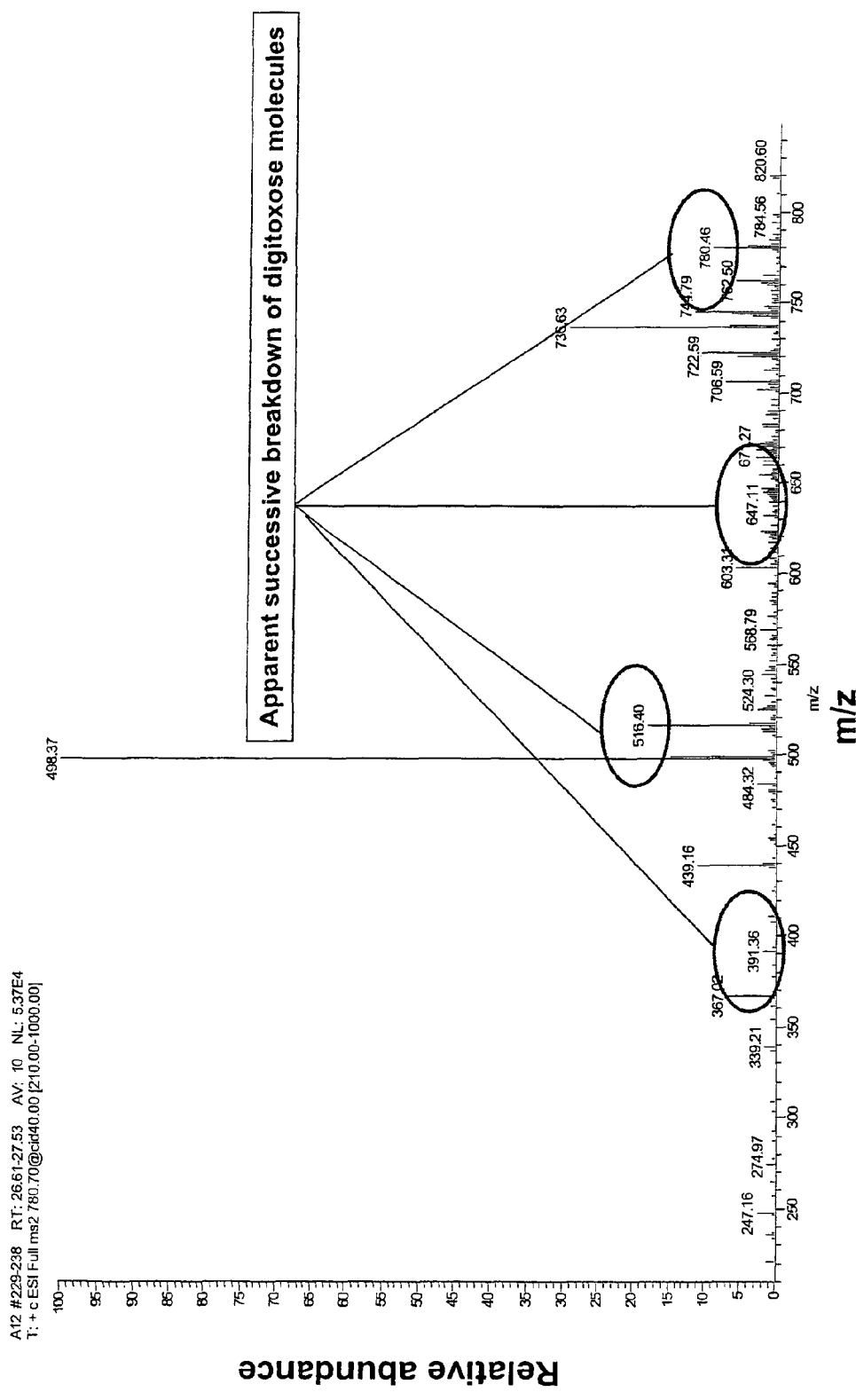

Total extracts from *Magnaporthe* wild-type or abc3Δ appressoria was isolated and tested for antifungal activity against *S. pombe*. Cell density, in terms of absorbance at 600 nm, of cells in presence or absence of total appressorial extract was measured after every 1 h over 5 to 6 generations (15 to 18 h). The growth kinetics showed inhibitory effects of the crude extracts from the abc3Δ appressoria as compared to that from wild-type. This inhibitory activity was used as a tool to guide the purification of the presumable efflux target of Abc3p. Chromatographic fractionation of the appressorial extracts from abc3Δ showed a range of molecules eluting out based on their respective sizes. These molecules were collected in different fractions using an automated fraction collector. Molecule(s) of very small size (eluted in fraction number 16 and 17) (FIG. 1a) among all the fractions collected was found to be the most effective in terms of cytotoxicity toward fission yeast cells. The molecules in fraction 16 and 17 were further separated on HiTrap column and tested for their cytotoxic activity against fission yeast. Fraction number 9 to 16 therein (FIG. 1b) showed similar cytotoxic activity against yeast and were pooled and purified using C18 RP-HPLC column. Liquid chromatographic separation of fraction 9 to 16 on the HPLC column showed a single prominent UV (220 nm) peak which was eluted in fraction number 12 (FIG. 1c). Mass spectrometric analysis by soft ionization of this molecule in fraction 12 indicated a major m/z 780 species (FIG. 2a). Reference and compound library searches indicated that Digoxin, a cardiac glycoside from foxglove plant, with a steroid nucleus, sugar side chain, and a lactone ring, has a similar m/z 780 (FIG. 2b) (Qazzaz et al. 1996). Tandem mass spectrometric analysis of m/z 780 species from fraction 12 showed daughter ions of various m/z including m/z 647, 516, and 391 (FIG. 2c). Mass spectrometric analysis of Digoxin shows daughter ions including m/z 650, 520, and 390, which are successive breakdown products of digitoxose molecules. ELISA tests using monoclonal anti-digoxin antisera confirmed the immuno-reactivity of ATS towards anti-digoxin antibodies. The concentration of ATS in HPLC-purified samples was estimated to be 0.2 ng/gl. In humans, digoxin is effluxed by a P-glycoprotein. By inference, the inhibitory molecule (ATS) present in fraction 12 was therefore considered to be digoxin-like glycoside.

Example 12

ATS Affects Cytokinesis in *S. pombe*

Figure 3A:
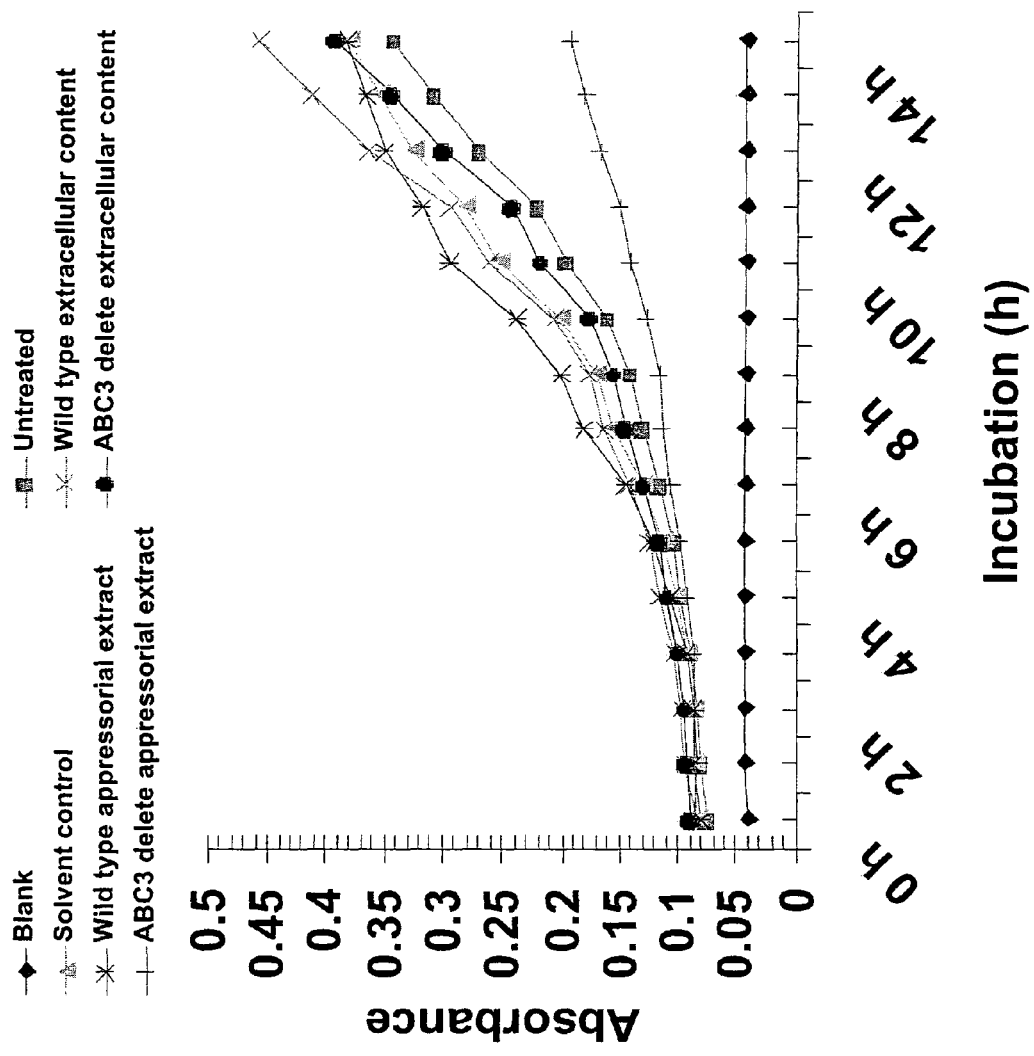
FIG. 3: Antifungal activity of ATS. a) Cell density of wild-type *S. pombe* cells was measured in terms of absorbance in presence of wild-type or abc3Δ appressorial extract. b) ATS treated or untreated wild-type *S. pombe* cells were stained with calcofluor white (CFW) after 6 h of incubation. Arrows show septal deposition defect in treated cells. Bar=10 μm. c) *S. pombe* strain expressing histone-GFP were treated with ATS or solvent for 6 h and processed for epifluorescent microscopic detection. Arrows indicate defects in the nuclear structure. The same set of cells were also stained with CFW and examined for defects in septal deposition (arrows). Bar=5 μm.
Figure 3B:
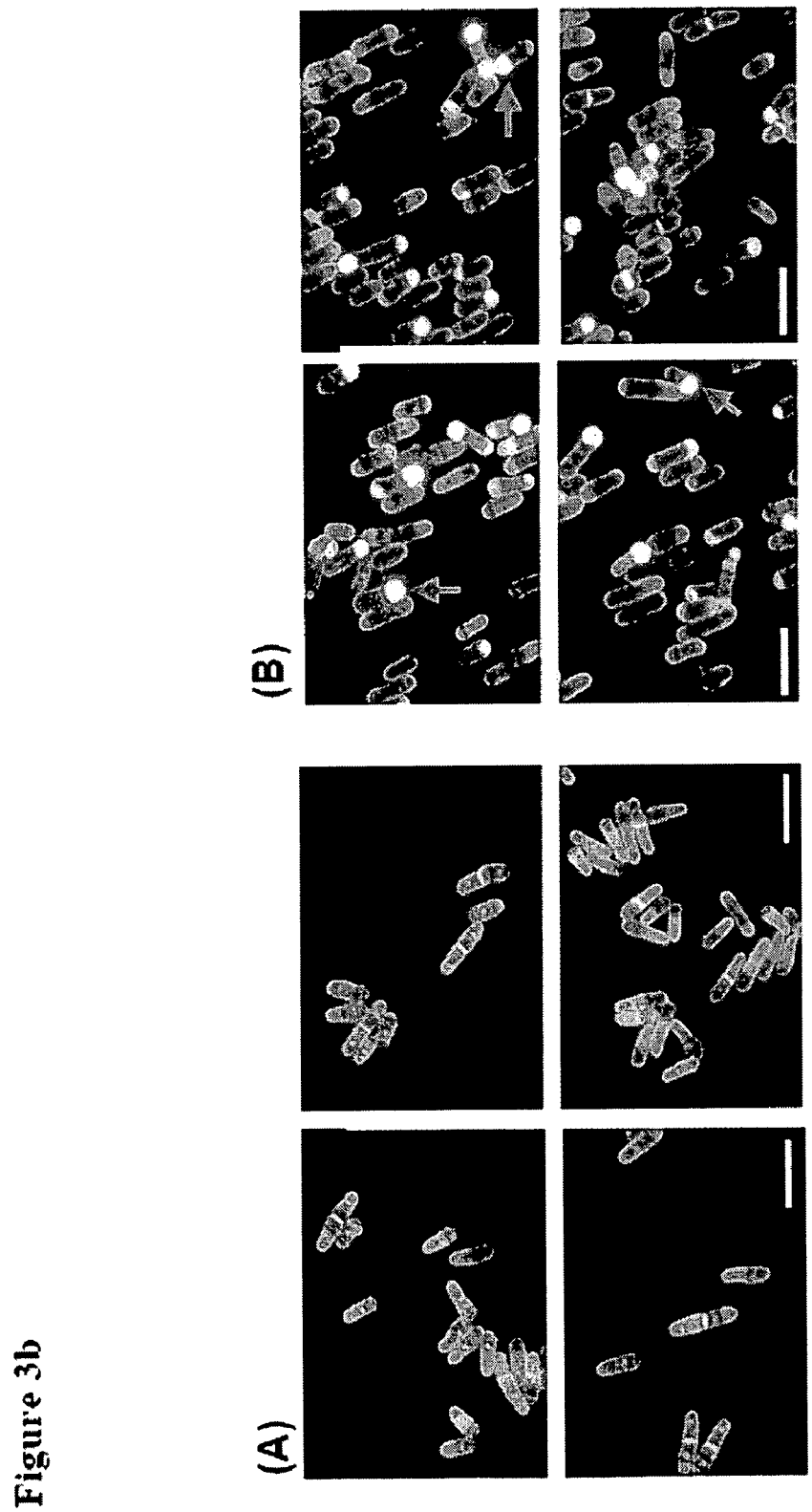
Figure 3C:
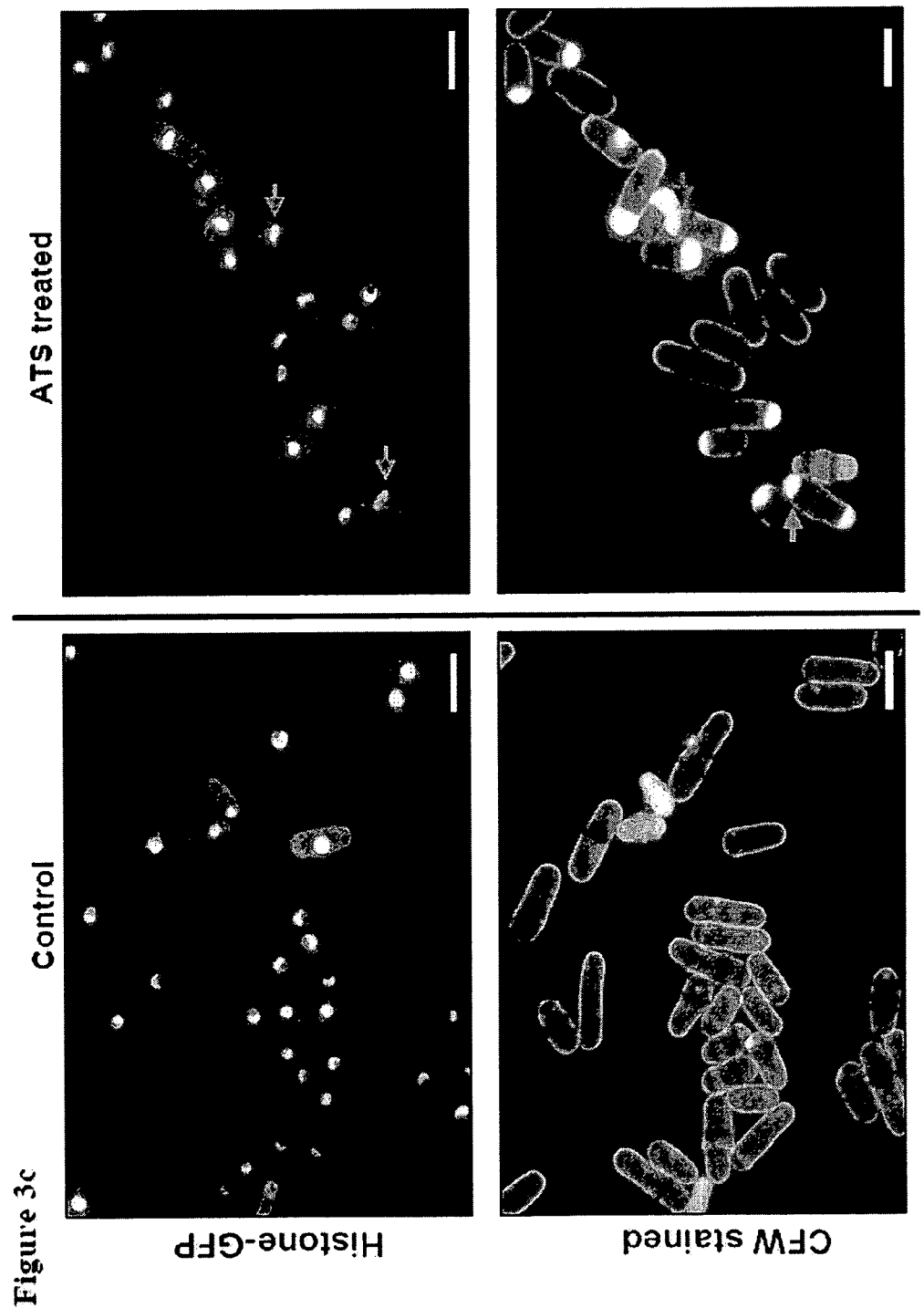

In an in vitro bioassay, *S. pombe* cells were grown in the absence or presence of ATS or crude abc3Δ appressorial extract and observed over a period of 8 to 10 h. Growth kinetics showed that the cell density ($OD_{600\ nm}$) dropped significantly when treated with ATS or crude abc3Δ appressoial extract (FIG. 3a). The cell density started decreasing at 4 h of ATS treatment; whereas the yeast cells treated with the appressorial extract from the wild-type *Magnaporthe* showed cell density similar to the untreated control. Microscopic observation of the ATS-treated and calcofluor-stained cells showed that ATS affects biogenesis of cell wall and/or septa in *S. pombe*. ATS-treated cells were elongated, enlarged in size and showed aberrant and unipolar deposits of excessive septum/cell wall material at the cell tip. One of the ends of the affected cells showed surplus staining with CFW indicating derailment of and excess septal deposition at one cell end unlike untreated cells (FIG. 3b). Similarly, *S. pombe* cells expressing Histone-GFP were challenged with ATS and the assays showed that ATS also had a significant effect on nuclear division in *S. pombe* (FIG. 3c). Growth kinetics indicated that incubation for 6 h was enough to observe these profound effects of ATS in fission yeast.

Example 13

Digoxin, Digoxigenin, and Ouabain Show Anti-Fungal Activity

Figure 4A:
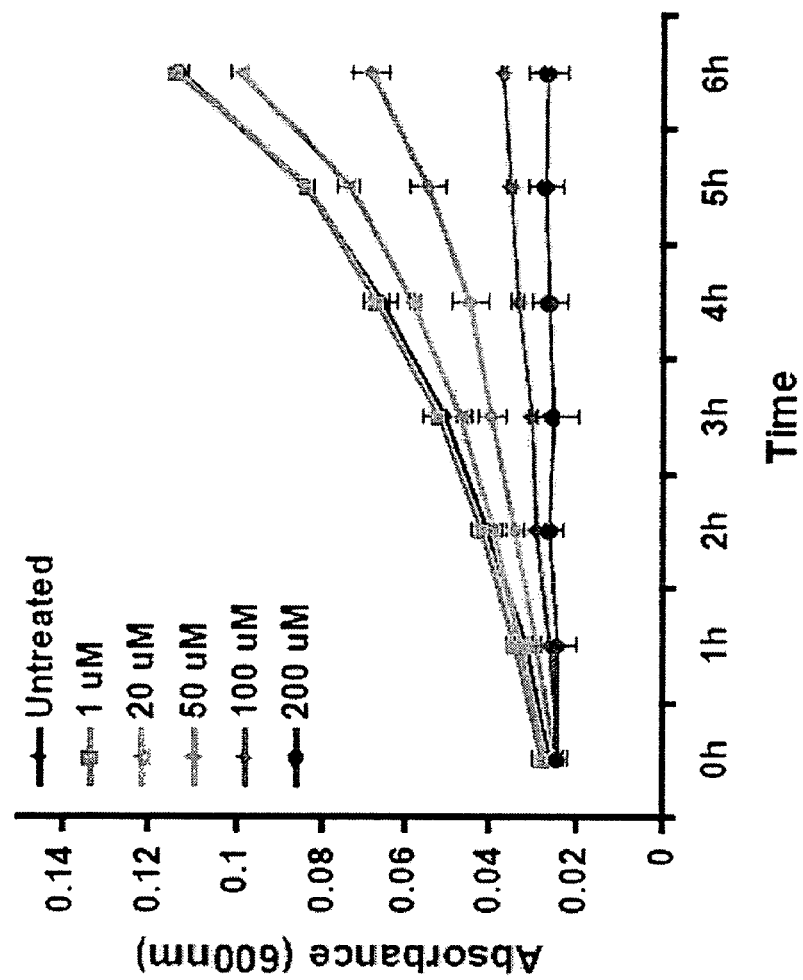
FIG. 4: Antifungal activity of digoxin, digoxigenin, and ouabain. Cell density of wild-type *S. pombe* was measured in terms of absorbance at 600 nm in absence or presence of different concentrations of digoxin (a), digoxigenin (b) or ouabain (c). The data for the activity of digoxin represent mean±SE of at least two independent experiments.
Figure 4B:
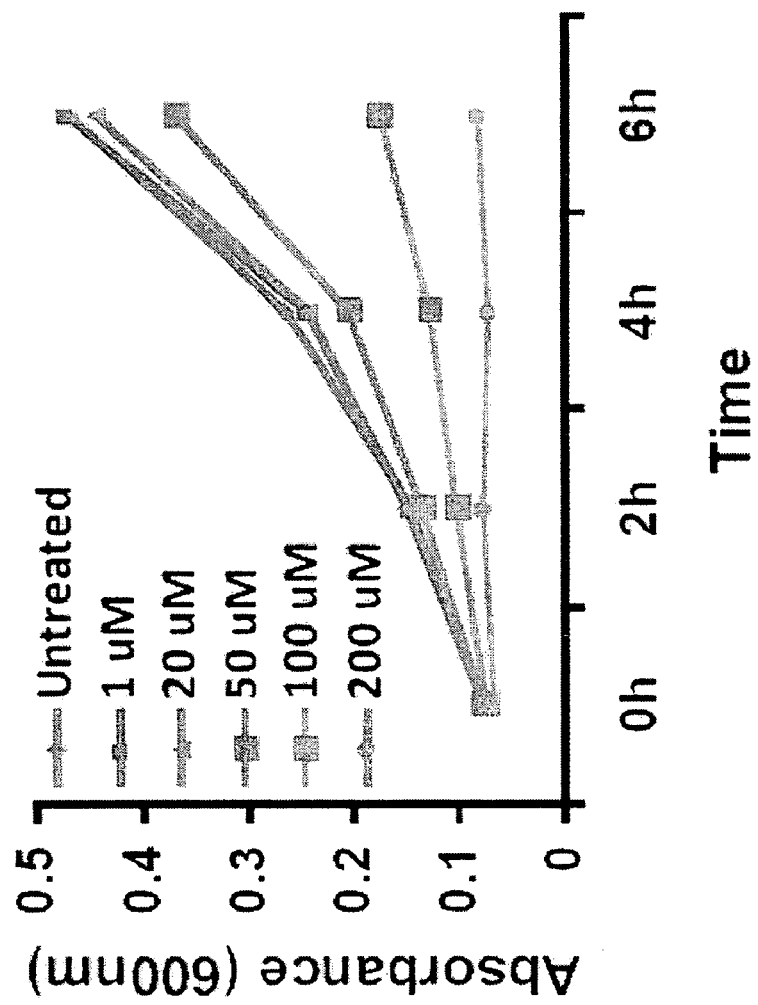
Figure 4C:
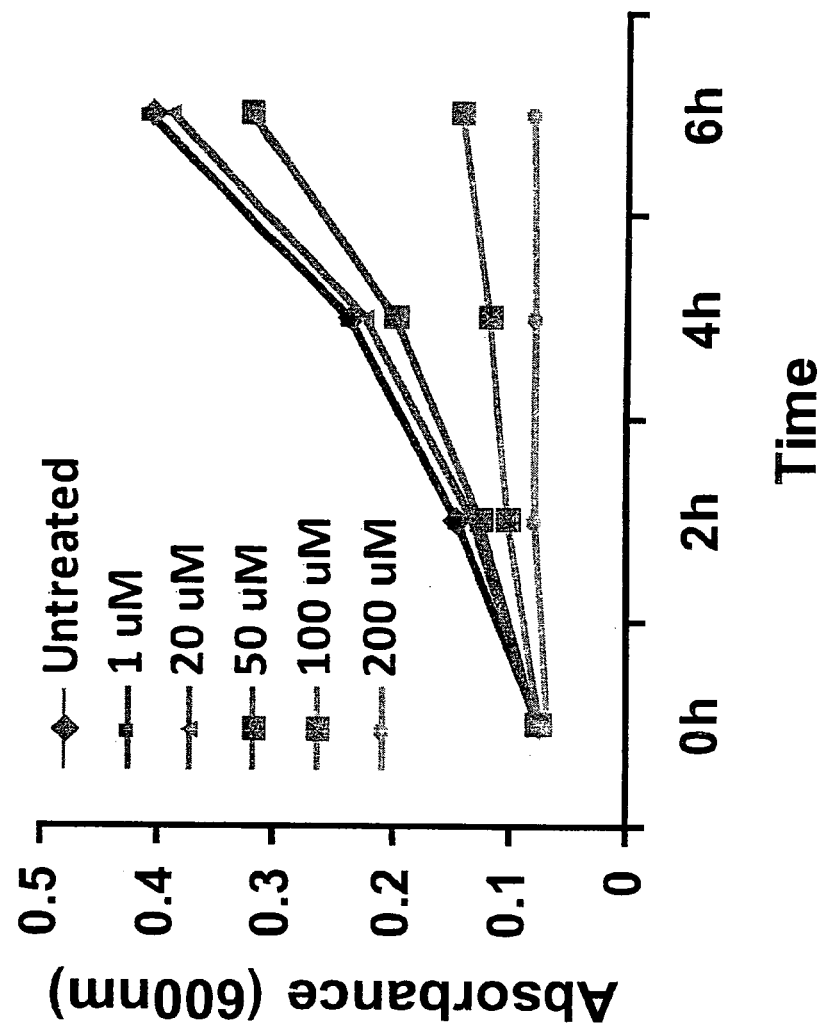

Wild-type *S. pombe* cells were grown in absence or presence of different concentrations of digoxin, digoxigenin, or ouabain and growth kinetics was studied over 6-8 h. While untreated cells showed increase in cell density over 6 h of incubation, digoxin treated cells showed decrease in absorbance in a dose dependent manner. The minimum concentration of digoxin (FIG. 4a), digoxigenin (FIG. 4b), or ouabain (FIG. 4c) required to completely inhibit growth in *S. pombe* cells was found to be between 100 to 200 µM.

Example 14

ATS is Specifically Effluxed by *M. grisea* Abc3p

Figure 5:
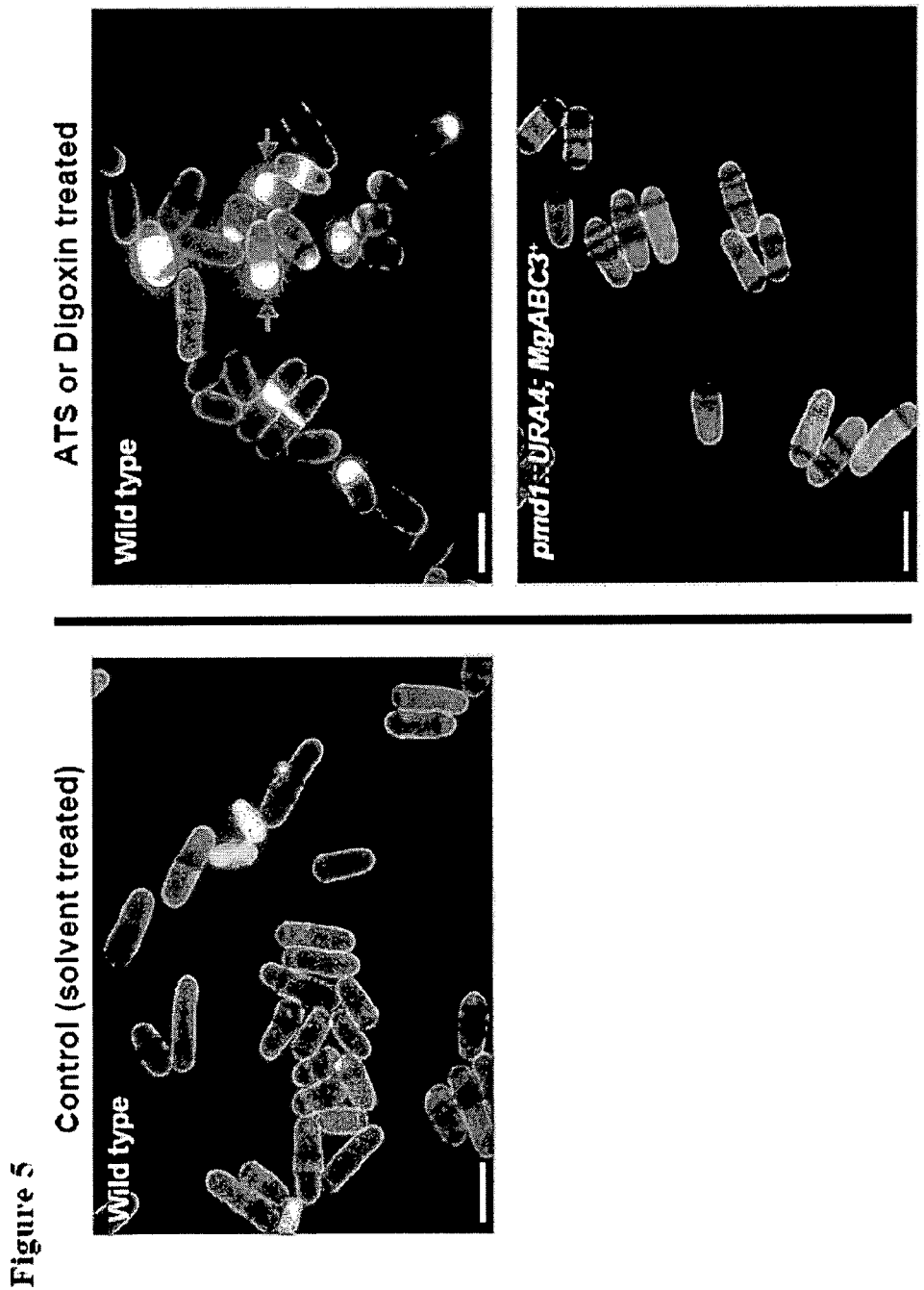
FIG. 5: ATS is a specific efflux target of *Magnaporthe* Abc3p. *S. pombe* wild-type and strain expressing *M. grisea* Abc3 were treated with ATS or residual solvent and were stained with CFW after 6 h. Bar=5 μm.

*S. pombe* strain expressing *Magnaporthe* ABC3 (MBY 2838) was used to test the effect of ATS. Importantly, the MBY 2838 cells were not affected by the presence of ATS in the growth medium. Such ATS-treated MBY 2838 cells showed normal cytokinesis with normal cell size and shape like the untreated control cells of S. pombe (FIG. 5). These findings strongly suggest that ATS is most likely an efflux target of the Abc3 transporter in Magnaporthe.

Example 15

ATS Causes Morphological Changes in C. albicans

Figure 6:
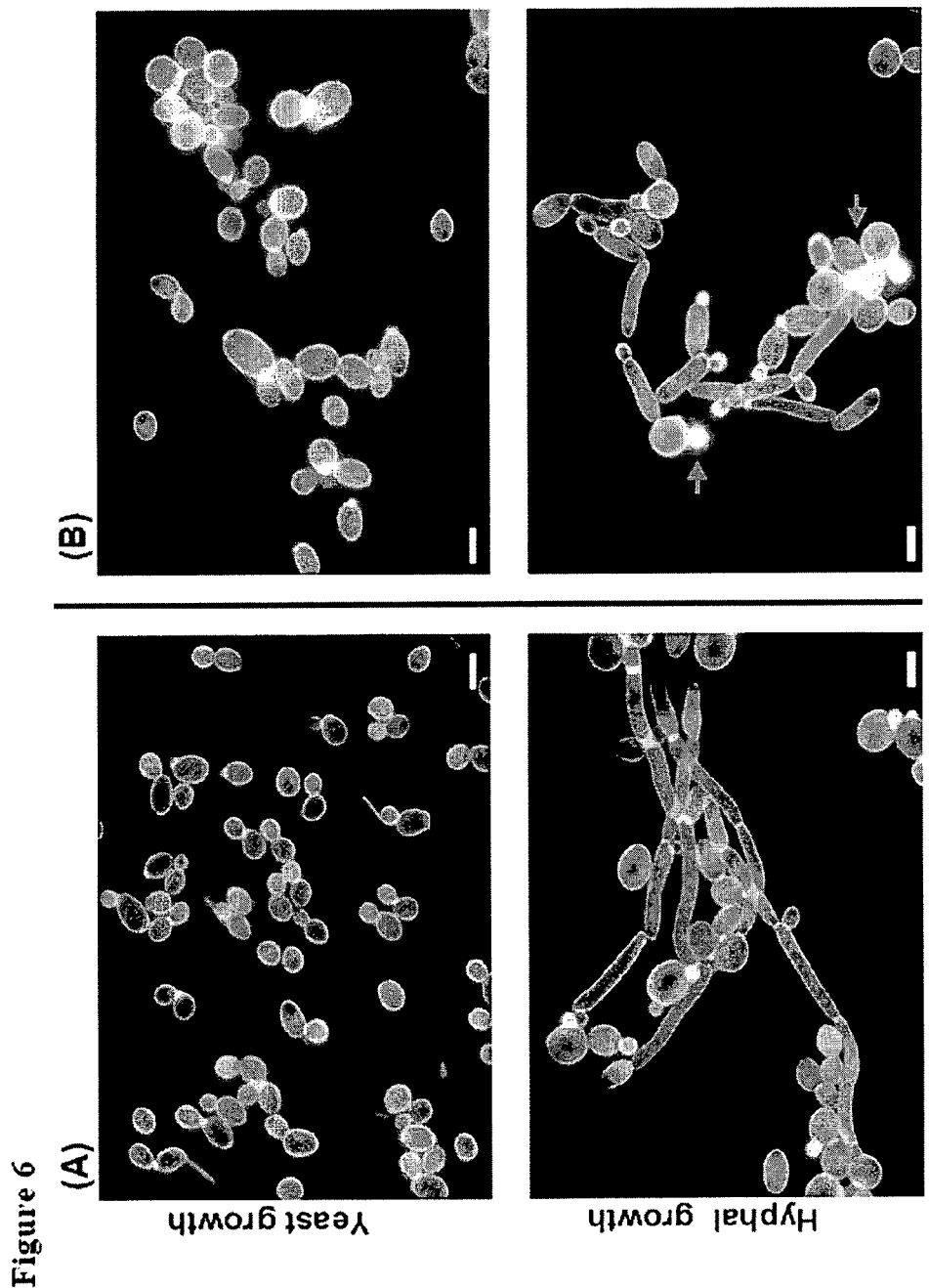
FIG. 6: ATS leads to pseudohyphal development in *Candida albicans*. Panel (A) shows CFW-stained wild-type untreated yeast (upper panel) or true-hyphal (lower panel) growth of *C. albicans*. Panel (B) shows *C. albicans* treated with ATS for 6 h and stained with CFW. Arrows show septal deposition defect in the treated cells. Bar=10 μm.

Wild-type C. albicans strain SC5314 was grown in the absence (untreated) or presence of ATS in order to study its cytotoxic activity. Both yeast and hyphal form of C. albicans were studied in this assay. The cells were incubated for 6 h with ATS and stained with Calcofluor White. Microscopic studies of the treated yeast cells showed defects in morphology in terms of elongation and enlargement of the cells. The treated yeast cells also showed excess cell wall/septal deposits especially at the budding site and over the entire periphery. Similarly, ATS showed strong effects on hyphal cells in Candida resulting in shorter and aberrant hyphal extensions that failed to advance in growth. Moreover, excess cell wall staining by CFW was also seen in case of ATS-treated hyphal cells compared to the control or untreated cells (FIG. 6).

Example 16

ATS Prevents Wild-Type M. grisea from Breaching the Host Surface

Figure 7A:
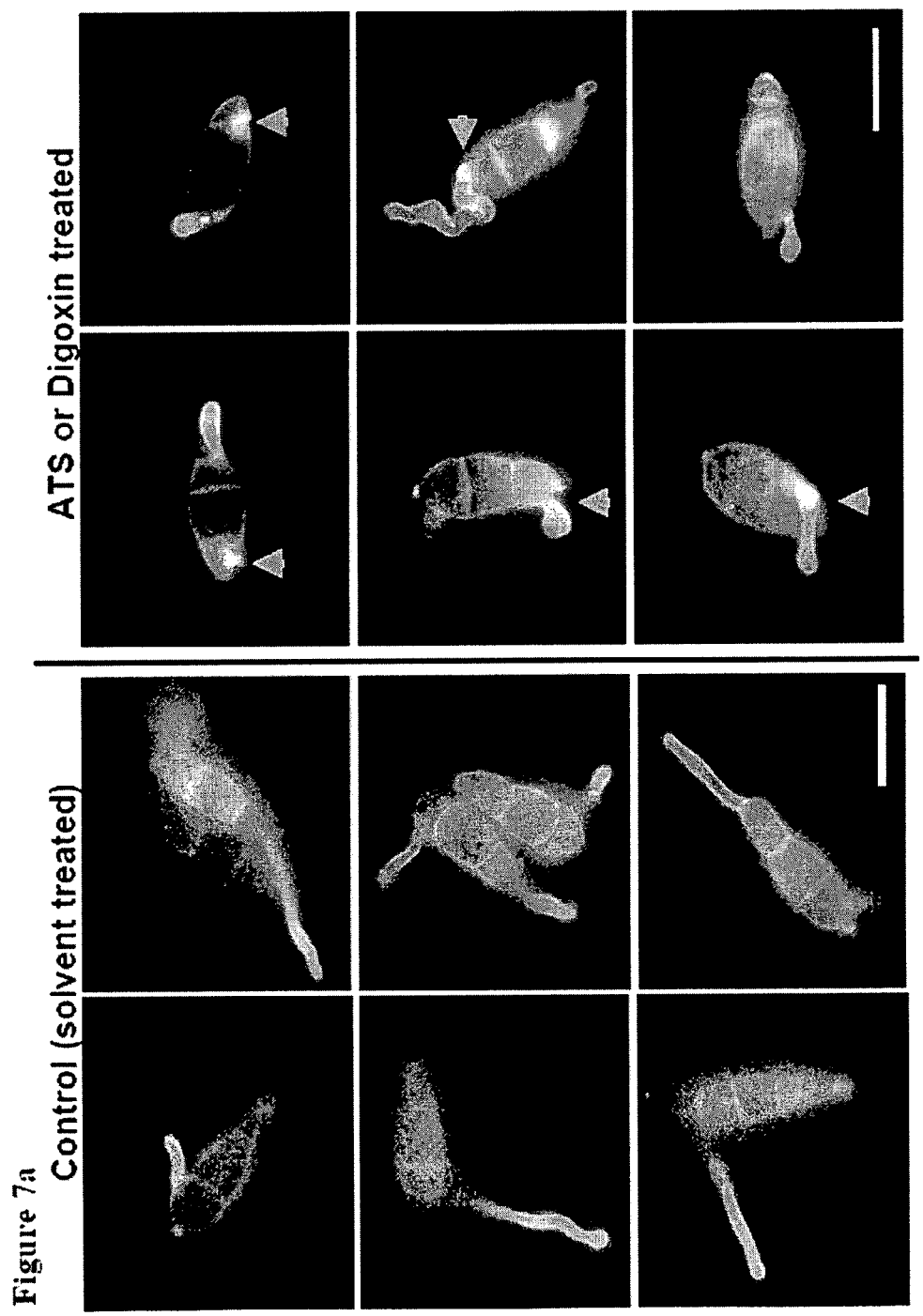
FIG. 7: Effect of ATS on *M. grisea*. a) Wild-type *Magnaporthe* Guy11 strain was germinated in the presence or absence of ATS for 2-3 h and stained with CFW. Bar=5 μm. b) Panel (A) shows appressorial function assessed as papillary callose deposits (%; white arrows) after 24 h in untreated or ATS-treated *M. grisea*, respectively. Asterisk indicates the rare callose deposition in ATS-treated appressoria. Panel B shows DIC images of inoculated rice leaf sheath after 30 h. Arrowheads indicate appressoria that lacked invasive hyphae. Bar=10 μm. Panel (C) shows the quantification of the appressorial function (as in A) in untreated or ATS-treated *M. grisea* on barley leaf explants. Data (presented as Mean±SE) was derived from three replicates.
Figure 8A:
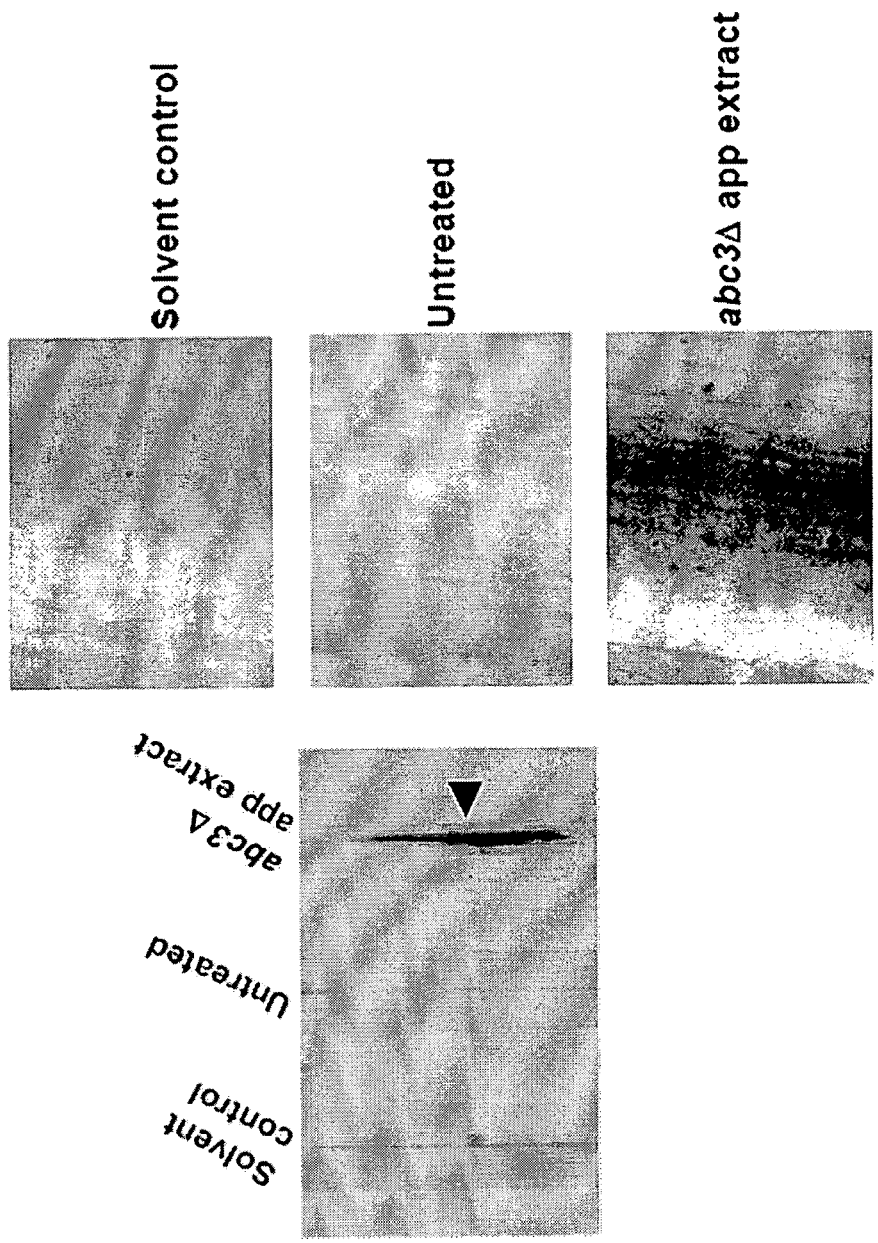
FIG. 8: ATS elicits HR-like response in rice. a) ATS-treated or untreated barley leaf explant was stained with trypan blue and observed under bright field. Arrowhead shows visible HR-like cell death. b) ATS-treated or untreated rice leaf explant was stained with $CeCl_3$ and observed by electron microscopy. Red or white arrows indicate cerium perhydroxide granules. Red arrows indicate plasmolysis after ATS treatment for 48 h. CW, cell wall; M, mitochondrion; and V, vacuole. Bar=1 μm.
Figure 8B:
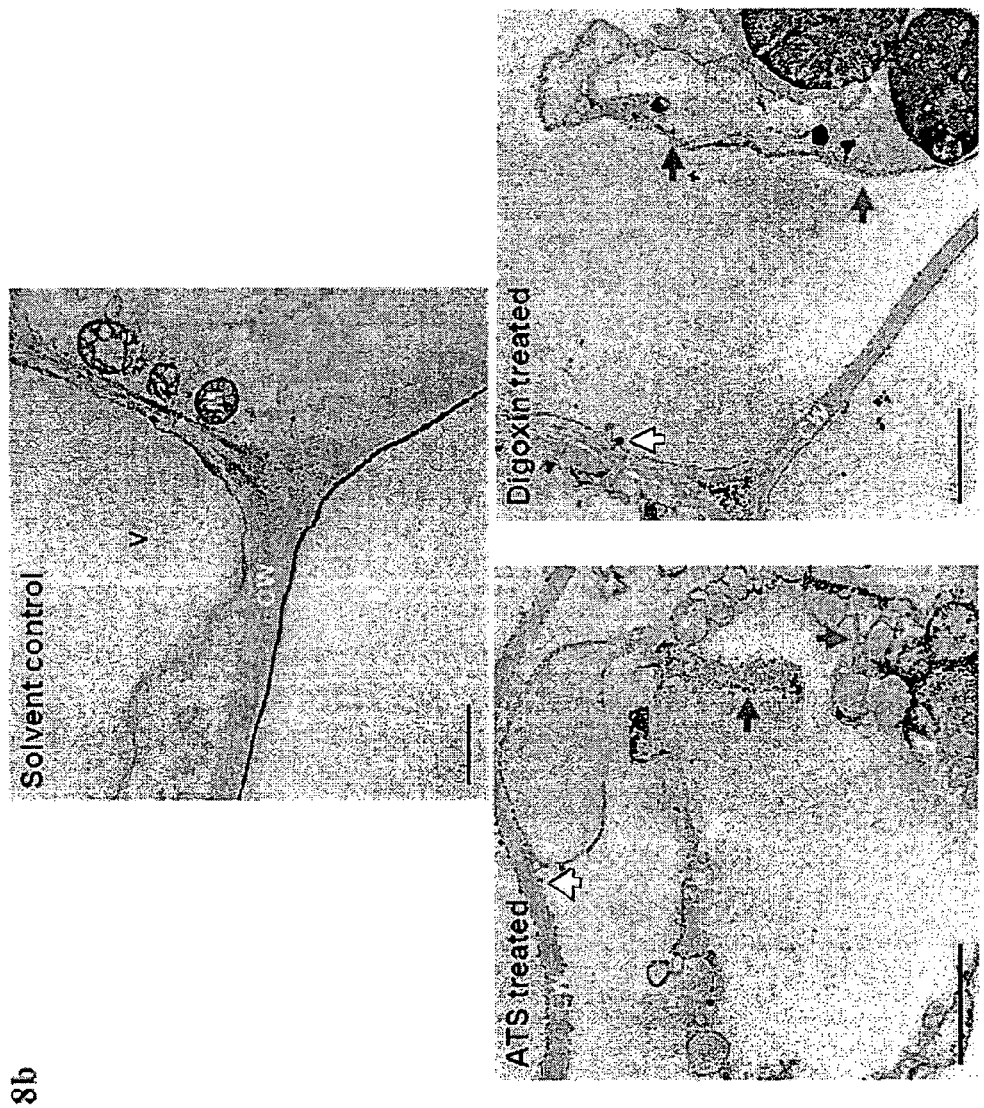
Figure 9:
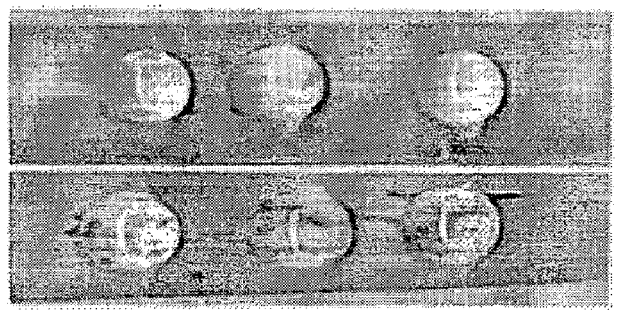
FIG. 9: Digoxin reduces *Magnaporthe* infection in barley. Detached barley leaf pieces were inoculated with 100 or 200 conidia per drop in presence or absence of 200 μM digoxin. The disease reaction was scored on 6 dpi. The data represent observations from 3 independent experiments.
Figure 10:
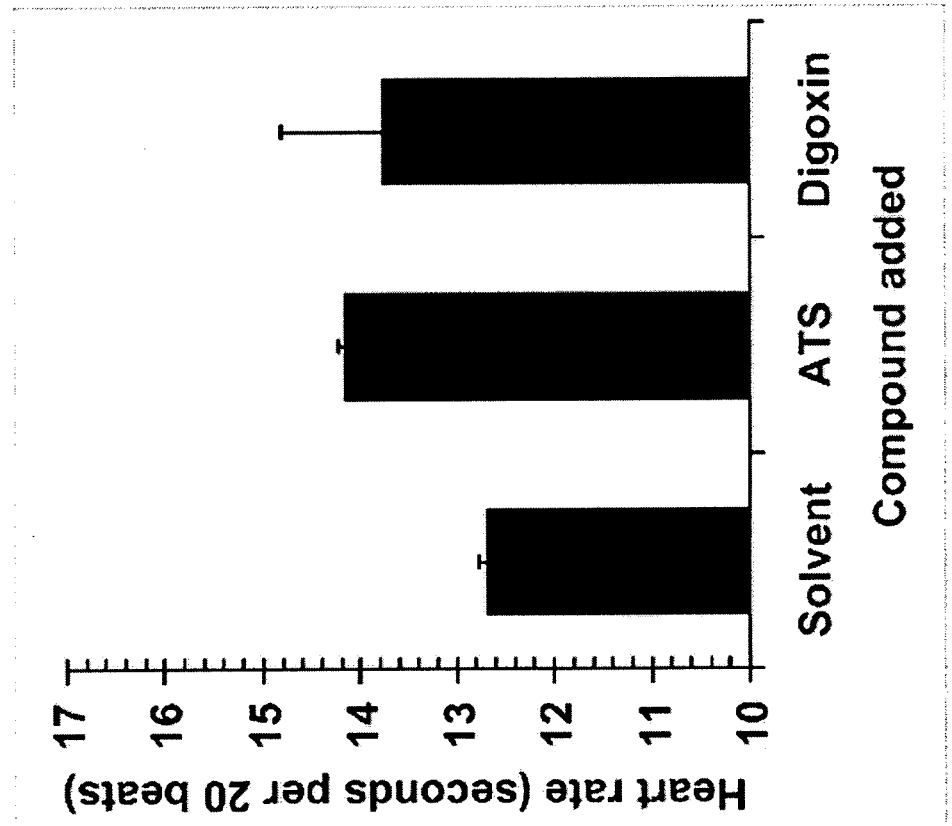
FIG. 10: Effect of ATS on cardiac activity in Zebra fish. Zebra fish embryos were incubated in the presence of ~415 nM ATS (in fish water) or residual solvent and observed under bright field microscope to monitor heart development and function over 3 days post fertilization. Bar chart showing the heart rates of the larvae treated with ATS or Digoxin or residual solvent. Heart rate was measured as seconds per 20 beats after 26 h of treatment. The data represent mean±SE from three independent experiments.

Germination of M. grisea in presence of ATS showed that it did not inhibit germination and subsequent development into appressorium on inductive surfaces. However, the germ tubes showed morphological defects upon the addition of ATS, culminating in relatively shorter, curved moieties with excessive septal deposits at the point of germ tube emergence (FIG. 7a). Successful penetration of onion epidermis or rice leaf sheath by M. grisea was assessed by observing callose deposition and penetration hyphae within the host tissue. Aniline blue staining for callose deposition after 24 h post inoculation showed that almost 52% of the wild-type untreated appressoria had successfully penetrated the host cells; whereas only 14% of the ATS-treated wild-type appressoria were able to induce callose deposition in the host tissue. Microscopic analysis after 30 h revealed that about 60% of the untreated appressoria developed infection hyphae within the host cells; whereas those were seen in only 3-4% of the ATS-treated appressoria (FIG. 7*b*). These results suggest that ATS has a direct inhibitory action and reduces Magnaporthe invasion into the host plants.

Example 17

ATS Elicits Hypersensitive Response in Rice

Exogenous application of ATS or Digoxin to leaf tissue was examined to study its effect on the host plant. Cell viability tests using trypan blue staining of rice or barley leaf tissue showed hypersensitive reaction (HR) like visible cell death after 48 to 72 h in case of the ATS inoculated tissue in contrast to the control or uninoculated samples (FIG. 8*a*). Elevation in the levels of $H_2O_2$ was studied in treated and untreated leaf tissues by TEM analysis after staining them with Cerium chloride ($CeCl_3$). Both Digoxin- or ATS-treated leaf tissues showed accumulation of Cerium perhydroxide precipitate in the cell wall and cell membrane. Moreover, the host cells showed plasmolysis upon treatment with Digoxin or ATS, indicating programmed-like cell death upon treatment. The control leaf tissue, however, did not show any plasmolysis or increased accumulation of Cerium perhydroxide precipitate (FIG. 8*b*). Thus, ATS or Digoxin showed elicitor-like functions and induced hypersensitive reaction or disease resistance type of response in the host plants.

Example 18

Digoxin Reduces Blast Disease Symptoms

Detached barley leaf pieces were inoculated with *Magnaporthe* conidia (ca 100) in the presence or absence of digoxin, and the disease reaction scored for lesions after 6 days. The control leaf pieces without digoxin started developing disease symptoms on day 3. However, equivalent number of conidia in the presence of 200 μM digoxin failed to elicit any disease symptoms. On day 6 post inoculation, the severity of disease in the presence of digoxin was significantly reduced compared to control leaves. Importantly, the leaves inoculated with 100 conidia per droplet did not show any symptoms in the presence of digoxin even after 6 dpi, whereas the inoculum lacking digoxin showed significant disease lesions (FIG. 9). Digoxin (and, similarly, digoxigenin, ouabain, and ATS), therefore, are potentially useful in controlling fungal diseases in plants.

Example 19

Excess ATS Reduces Heart Rate in Zebra Fish

Zebra fish embryos treated with ~100 ng of ATS showed no obvious effect on the development of the larvae. However, the most prominent and specific effect was seen on the cardiac rhythm in the ATS-treated larvae. The estimation of heart rates (time in seconds taken for 20 beats) in the presence of ATS or Digoxin revealed slower heart rate compared to normal or residual solvent treated samples until 48 hours post fertilization (hpf). At 26 heart rates were found to be 12.71, 14.18, and 13.79 seconds for control, ATS, and digoxin-treated larvae, respectively (FIG. 10). At 48 hpf, the heart rate was estimated to be 9.95 and 11.33 seconds for 20 beats for the control and ATS-treated larvae, respectively. At concentrations lower than above i.e. 50, 25, or 10 ng, the larvae showed decreasing effect of ATS with normal heart rate. Thus, ATS, at nanomolar concentrations, may have a good potential therapeutic use in treating cardiac arrhythmia.

In the present invention, we have successfully isolated and purified a novel cytotoxic metabolite, ATS, from *M. grisea* making it an attractive model for drug discovery and for metabolite and toxicological studies. The cytotoxic effect on fission yeast, *Candida* spps, and a phytopathogenic fungus showed that ATS has an inherent broad spectrum antifungal activity. The fission-yeast based assay used to guide purification of this cytotoxic compound in the present work, promises to be a robust and efficient method for screening and/or evaluating novel drugs.

The specific inhibition of host penetration by the plant pathogen *Magnaporthe*, and induction of hypersensitive response in the host plant by ATS or digoxin suggests their potential application in agriculture in controlling fungal disease(s) of important crop plants. It also has been demonstrated herein that digoxin and related cardiac glycosides, such as digoxigenin and ouabain, possess significant antifungal activity and thus, are potentially useful as fungicides. Furthermore, our preliminary results on the effects of ATS on cardiac activity in zebra fish point out its potential therapeutic use in treating arrhythmia.

A combination of size exclusion chromatography and fast performance liquid chromatography (FPLC) was used to purify the ATS metabolite from *M. grisea*. The effect of ATS on cytokinesis in *Schizosaccharomyces pombe*, and host penetration by *Magnaporthe*, were used as bioassays for the isolation of ATS from abc3Δ mutant. Purified ATS was analyzed by electrospray ionization-tandem mass spectrometry (ESI-MS/MS) technique. ATS or digoxin showed inhibitory effects on *S. pombe* likely due to mitotic defects and faulty septal depositions during cell division. *S. pombe* expressing *M. grisea* Abc3p did not show any effects of ATS or Digoxin. Interestingly, ATS treatment led to morphogenetic defects such as cell elongation and restricted hyphal extension in the opportunistic fungal pathogen *Candida albicans*. ATS-treated *M. grisea* showed aberrant septal deposition in the germ tubes and ATS (or Digoxin) treatment blocked appressorial function of host penetration. Furthermore, ATS or Digoxin induced hypersensitive reaction in rice leaf tissue likely due to elevated $H_2O_2$ in epidermal cells. Exogenous supply of excess ATS resulted in slower than normal heart rates in zebrafish larvae.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods, fish, organisms, and compositions of the instant invention can be incorporated in the form of a variety of embodiments, only a few of which are disclosed herein. Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

LIST OF REFERENCES

Bagnis, C. I., and Deray, G. (2002). Amphotericin-B nephrotoxicity. Saudi J Kidney Dis Transpl 13, 481-491.

Boucher, H. W., Groll, Chiou, C. C., and Walsh, T. J. (2004). Newer systemic antifungal agents: pharmacokinetics, safety and efficacy. Drugs 64, 1997-2020.

Buchaklian, A. H., and Klug, C. S. (2006). Characterization of the LSGGQ and H motifs from the *Escherichia coli* lipid A transporter MsbA. Biochemistry 45, 12539-12546.

Lee, J. Y., and Hwang, B. K. (2002). Diversity of antifungal actinomycetes in various vegetative soils of Korea. Can J Microbiol 48, 407-417.

Mimee, B., Labbe, C., Pelletier, R., and Belanger, R. R. (2005). Antifungal activity of flocculosin, a novel glycolipid isolated from *Pseudozyma flocculosa*. Antimicrob Agents Chemother 49, 1597-1599.

Osbourn, A. E. (1999). Antimicrobial phytoprotectants and fungal pathogens: a commentary. Fungal Genet Biol 26, 163-168.

Pastan, I. H., and Gottesman, M. M. (1988). Molecular biology of multidrug resistance in human cells. Important Adv Oncol, 3-16.

Qazzaz, H. M., Goudy, S. L., and Valdes, R., Jr. (1996). Deglycosylated products of endogenous digoxin-like immunoreactive factor in mammalian tissue. J Biol Chem 271, 8731-8737.

Rangaswamy, V., Jiralerspong, S., Parry, R., and Bender, C. L. (1998). Biosynthesis of the *Pseudomonas* polyketide coronafacic acid requires monofunctional and multifunctional polyketide synthase proteins. Proc Natl Acad Sci USA 95, 15469-15474.

Ritz, U., Drexler, I., Sutter, D., Abele, R., Huber, C., and Seliger, B. (2003). Impaired transporter associated with antigen processing (TAP) function attributable to a single amino acid alteration in the peptide TAP subunit TAP1. J Immunol 170, 941-946.

Strohl, W. R. (2000). The role of natural products in a modern drug discovery program. Drug Discov Today 5, 39-41.

Sun, C. B., Suresh, A., Deng, Y. Z., and Naqvi, N. I. (2006). A multidrug resistance transporter in *Magnaporthe* is required for host penetration and for survival during oxidative stress. Plant Cell 18, 3686-3705.

Tanaka, A., Christensen, M. J., Takemoto, D., Park, P., and Scott, B. (2006). Reactive oxygen species play a role in regulating a fungus-perennial ryegrass mutualistic interaction. Plant Cell 18, 1052-1066.

Tsuruo, T., Naito, M., Tomida, A., Fujita, N., Mashima, T., Sakamoto, H., and Haga, N. (2003). Molecular targeting therapy of cancer: drug resistance, apoptosis and survival signal. Cancer Sci 94, 15-21.

Wang H., Tang X., Liu J., Trautmann S., Balasundaram D., McCollum D., and Balasubramanian M. K. (2002). The Multiprotein Exocyst Complex is Essential for Cell Separation in *Schizosaccharomyces pombe*. Mol. Biol. Cell 13 (2), 515-529.

What is claimed:

1. A method of controlling a fungal blast disease in a plant, said method comprising treatment of the plant with ABC3 Transporter Substrate (ATS) or a cardiac glycoside.

2. The method of claim 1, wherein the cardiac glycoside is selected from the group consisting of digoxin, digoxigenin, and ouabain.

3. The method of claim 1, wherein the plant is a crop plant.

4. The method of claim 3, wherein the crop plant is a monocot or a dicot.

5. The method of claim 3, wherein the crop plant is rice.

6. The method of claim 1, wherein the fungal blast disease is rice blast.

7. The method of claim 1, wherein said treatment induces a hypersensitive response in the plant.

8. The method of claim 1, wherein said treatment causes inhibition of host penetration by the fungal pathogen.

9. The method of claim 1, wherein the fungal blast disease is barley blast.

10. The method of claim 1, wherein the fungal blast disease is caused by *Magnaporthe grisea*.

* * * * *